(12) United States Patent
Bischoff

(10) Patent No.: US 6,271,208 B1
(45) Date of Patent: Aug. 7, 2001

(54) PROCESS OF MAKING CATIONIC LIPID-NUCLEIC ACID COMPLEXES

(75) Inventor: Rainer Bischoff, Barsebacksby (SE)

(73) Assignee: Transgene S.A., Strasbourg (FR)

( * ) Notice: Subject to any disclaimer, the term of this patent is extended or adjusted under 35 U.S.C. 154(b) by 0 days.

(21) Appl. No.: 09/254,149

(22) PCT Filed: Aug. 25, 1997

(86) PCT No.: PCT/IB97/01030

§ 371 Date: Feb. 26, 1999

§ 102(e) Date: Feb. 26, 1999

(87) PCT Pub. No.: WO98/08489

PCT Pub. Date: Mar. 5, 1998

(30) Foreign Application Priority Data

Aug. 26, 1996 (EP) .................................................. 96401819

(51) Int. Cl.[7] .................................................. A61K 31/70
(52) U.S. Cl. ........................................... 514/44; 536/23.1
(58) Field of Search .................................................. 514/44

(56) References Cited

U.S. PATENT DOCUMENTS

| | | | |
|---|---|---|---|
| 5,705,385 | * 1/1998 | Bally et al. | 435/320.1 |
| 5,830,878 | * 11/1998 | Gorman et al. | 514/44 |
| 5,976,567 | * 11/1999 | Wheeler et al. | 424/450 |

FOREIGN PATENT DOCUMENTS

| | | |
|---|---|---|
| 91 05545 | 5/1991 | (WO) . |
| 93 05162 | 3/1993 | (WO) . |
| 94 22429 | 10/1994 | (WO) . |
| 96 34109 | 10/1996 | (WO) . |
| 9637194 | * 11/1996 | (WO) . |
| 96 40962 | 12/1996 | (WO) . |
| 96 40963 | 12/1996 | (WO) . |

OTHER PUBLICATIONS

Gao et al., "Potentiation of Cationic Liposome–Mediated Gene Delivery by Polycations," *Biochemistry*, 35(3), 1027–1036 (Jan. 23, 1996).*

Liu et al.(I), "New Cationic Lipid Formulations for Gene Transfer," *Pharmacetuical Research*, 13(12), 1856–1860 (1996).*

Liu et al.(II), "Effect of Non–Ionic Surfactants on the Formulation of DNA/Emulsion Complexes and Emulsion–Mediated Gene Transfer," *Pharmaceutical Research*, 13(11), 1642–1646 (1996).*

E.K. Watson et al., "Plasmid DNA is Protected Against Ultrasonic Cavitation–Induced Damage When Complexed to Cationic Liposomes", Journal of Pharmaceutical Sciences, vol. 85, No. 4, Apr. 1996, USA, pp. 427–433, XP000558752.

P.L. Felgner et al., "Lipofection: A highly efficient, lipid–mediated DNA–transfection procedure" Proceedings of the National Academy of Sciences, USA, vol. 84, Nov., '87 pp. 7413–7417, XP000602252.

* cited by examiner

*Primary Examiner*—Gary Geist
*Assistant Examiner*—L. E. Crane
(74) *Attorney, Agent, or Firm*—Burns, Doane, Swecker & Mathis, L.L.P.

(57) ABSTRACT

The invention is related to a method for preparing an homogenous suspension of stable lipid-nucleic acid complexes or particles, comprising: a) combining one or more cationic lipids, one or more colipids, and one or more stabilizing additives to form a lipid suspension, b) combining the lipid suspension with a nucleic acid to form a complex or a particle, and optionally c) subjecting the complex or particle to a sizing procedure. It also concerns an homogenous suspension produced notably by the above method.

35 Claims, 15 Drawing Sheets

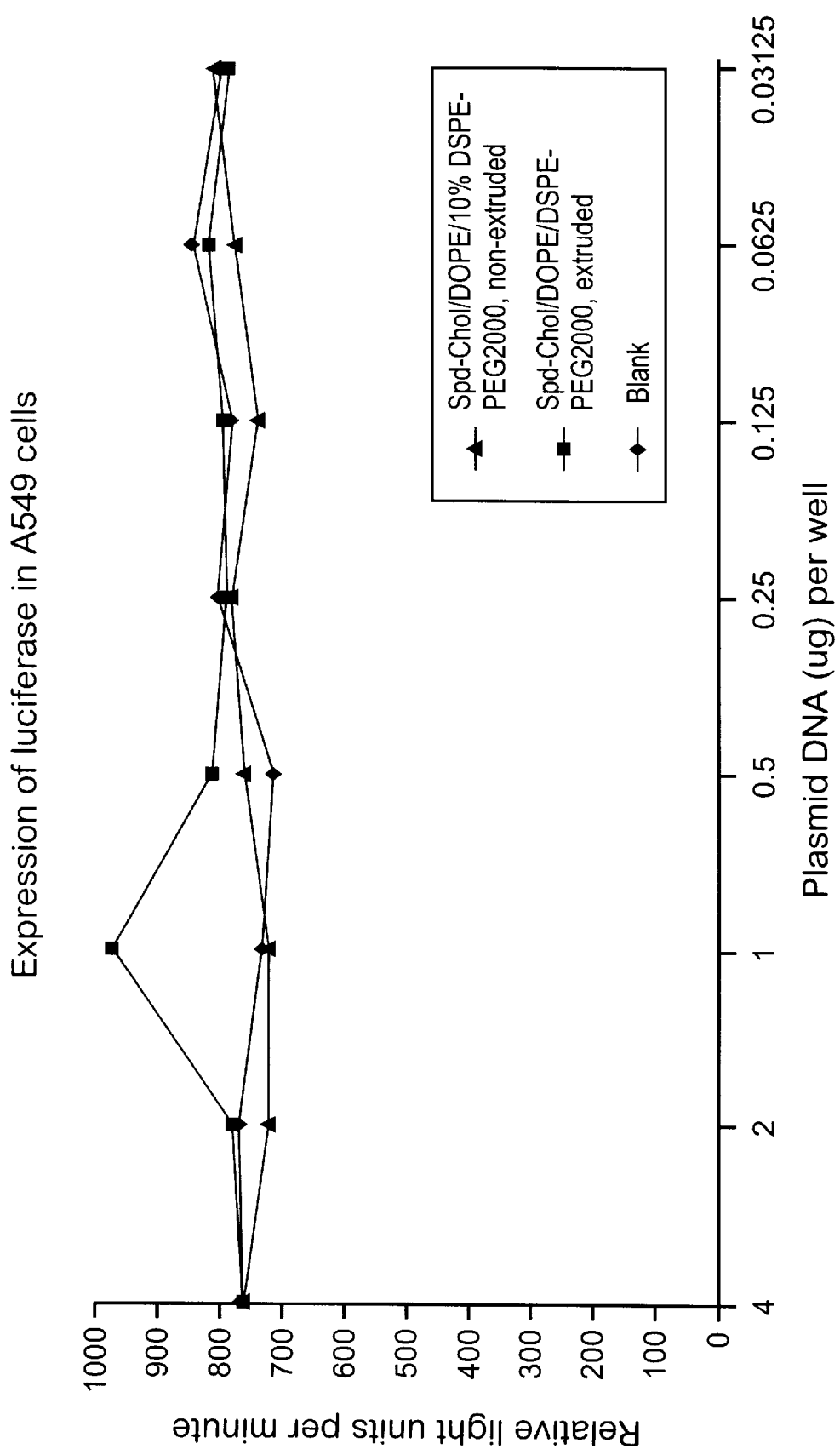

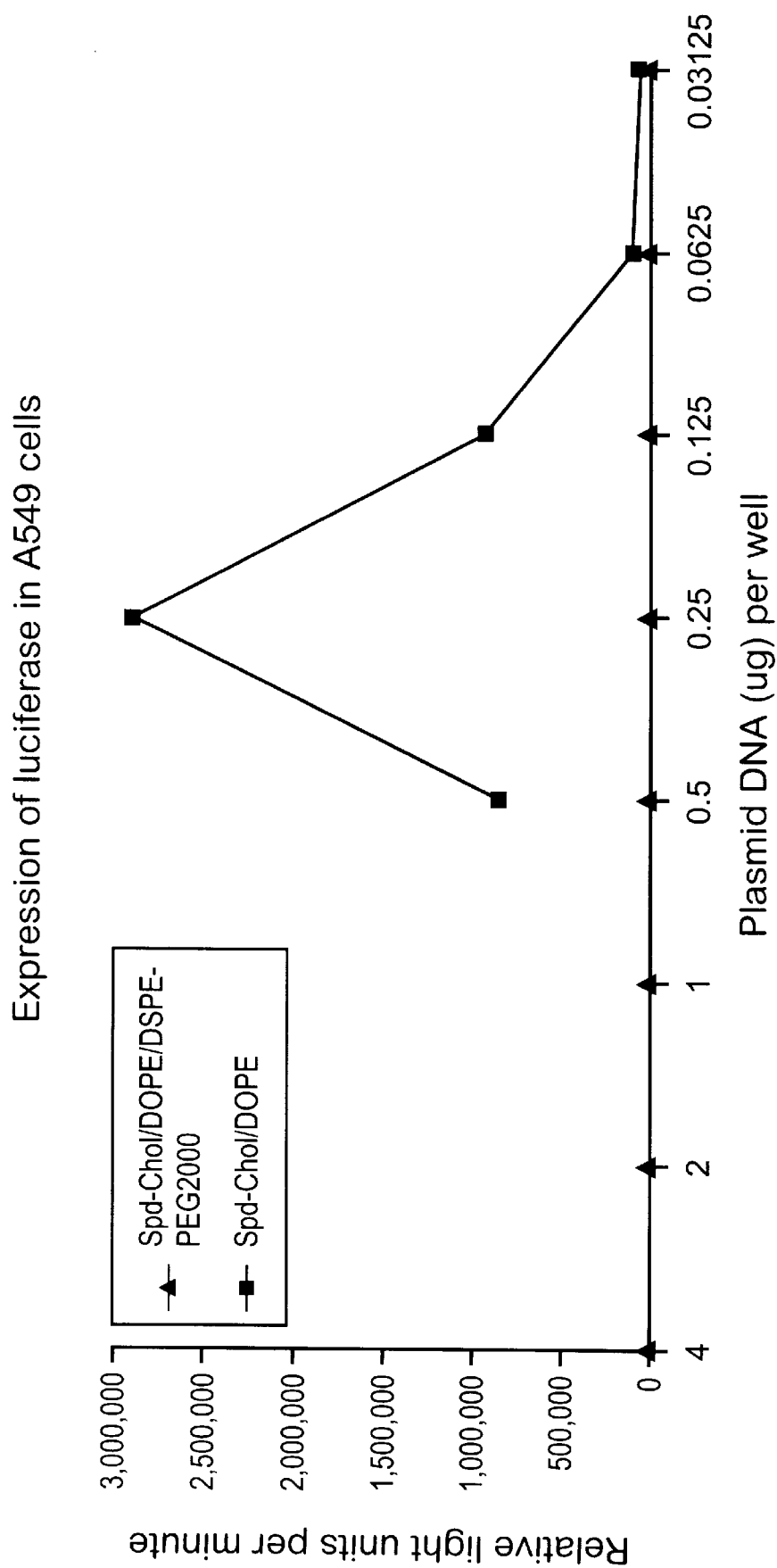

PROCESS OF MAKING CATIONIC LIPID-NUCLEIC ACID COMPLEXES

INTRODUCTION

The present invention is directed to stable complexes of cationic lipids and nucleic acid that can be used to deliver nucleic acid to a cell for the purpose of providing a therapeutic molecule to the cells of an individual in need of such treatment, and to methods for the preparation of stable, cationic lipid-nucleic acid complexes.

BACKGROUND OF THE INVENTION

Successful gene therapy depends on the efficient delivery to and expression of genetic information within the cells of a living organism. Most delivery mechanisms used so far involve viral vectors. Viruses have developed diverse and highly sophisticated mechanisms to achieve this goal including crossing of the cellular membrane, escape from lysosomal degradation, delivery of their genome to the nucleus and, consequently, have been used in many gene delivery applications.

Non-viral vectors, which are based on receptor-mediated mechanisms (Perales et al., Eur. J. Biochem. 226:255–266, 1994; Wagner et al., Advanced Drug Delivery Reviews 14:113–135, 1994) or on lipid-mediated transfection (Eelgner et al., Proc. Natl. Acad. Sci. U.S.A. 84:7413–7417 1987; Behr et al., Proc. Natl. Acad. Sci. U.S.A. 86:6982–6986, 1989; Gao et al., Biochem. Biophys. Res. Communic. 179:280–285, 1991; Behr, Bioconjugate Chemistry 5:382–389, 1994; Fahrhood et al., Annals New York Academy of Sciences, 716:23–35, 1994; Ledley, Human Gene Therapy 6:1129–1144, 1995) promise to have advantages with respect to large—scale production, reduced risks related to viral vectors, targeting of transfectable cells, lower immunogenicity and the capacity to deliver larger fragments of DNA.

The development of non-viral vectors for the delivery of nucleic acids into cells necessitates molecules that can associate with nucleic acids to allow these large, hydrophilic polyanions to cross the cell membrane, which is a hydrophobic, negatively charged barrier of a phospholipid bilayer, help them to escape from lysosomal degradation and facilitate their entry into the nucleus. Expression of the gene of interest also depends on the accessibility of the delivered nucleic acid to the cellular transcription machinery, most likely necessitating dissociation of the complexes.

Although having been described as early as 1965 (Bangham et al., J. Mol. Biol. 13:238–252, 1965), liposomes, which can encapsulate molecules of interest for delivery to -he cell, did not reach the marketplace as injectable therapeutics in humans until the 1990s (Gregoriadis, Trends in Biotechnol. 13:527–537, 1995). This delay is attributable to difficulties in obtaining reproducible formulations with acceptable stabilities. A major breakthrough was the development of "sterically stabilized (stealth) liposomes" which contained a certain percentage of polyethyleneglycol (PEG)-modified phospholipids (PEG-PLs) (Gregoriadis, Trends in Biotechnol. 13:527–537, 1995; Lasic, Angew. Chem. Int. Ed. Engl. 33:1685–1698, 1994). These PEG-PL containing liposomes proved to be more successful in evading detection and elimination by the reticulo-endothelial system, which resulted in greatly enhanced circulation half-lives. While (PEG)-modified liposomes have been most widely used, other hydrophilic polymers such as poly(vinyl pyrrolidone) which augment the stability of liposomes when grafted on their surface have been described (Torchilin, V. P. et al., Biochim. Biophys. Acta 1195:181–184, 1994).

Progress in lipid-mediated nucleic acid transfer into cells was advanced with the introduction of cationic lipids as vehicles for the transfer of nucleic acids into cells (Felgner et al., Proc. Natl. Acad. Sci. 84:7413–7417, 1987; Behr et al., Proc. Natl. Acad. Sci. 86:6982–6986, 1989; Gao et al., Biochem. Biophys. Res. Communic. 179:280–285, 1991; Behr, Bioconjugate Chemistry 5:382–389, 1994; Fahrhood et al., Annals New York Academy of Sciences 716:23–35, 1994; Ledley, Human Gene Therapy 6:1129–1144, 1995). Because cationic lipids are positively charged, they are able to complex with negatively charged nucleic acids. Unlike liposomes, these complexes do not require an encapsulation step and are prepared by simple mixing of components. The complexes essentially comprise of lipid-coated nucleic acid, in which the positively charged coat of the complex neutralizes the negative charges of the nucleic acid and, also, can efficiently bind to the negatively charged cell surface, facilitating entry of nucleic acid into the cell (Farhood et al., Annals N.Y. Acad. Sci. 716:23–35, 1994).

The advantages of using cationic lipids to mediate transfection of nucleic acids include the simplicity of preparation of the complexes, the ability of the lipid component to complex most of the nucleic acid, a wide range of cell types amenable to transfection, a high efficiency of transfer, lack of immunogenicity of the complexes and availability of the cationic lipids through chemical synthesis (Farhood et al., Annals N.Y. Acad. Sci. 716:23–35, 1994).

Cationic lipid-mediated delivery of nucleic acid to a wide variety of cell types has been demonstrated in vitro and in vivo. For example, nucleic acid encoding the cystic fibrosis transmembrane conductance regulator (CFTR) complexed with cationic lipids has been delivered to mouse lungs by intratracheal installation (Yoshimura et al., Nucleic Acids Res. 20:3233–3240, 1992) or by aerosol delivery (Stribling et al., Proc. Natl. Acad. Sci. 89:11277–1281, 1992). The delivery of CFTR using cationic lipids to a mouse model of cystic fibrosis (CF) produced correction of the ion channel defect (Hyde et al., Nature 362:250–255, 1993). Human clinical studies with cationic lipid-mediated delivery of the CFTR gene to CF patients demonstrated expression of the gene in nasal epithelium and no adverse clinical effects (Caplen et al., Nature Medicine 1:39–46, 1995).

Systemic gene expression of a reporter gene following a single intravenous injection of a cationic lipid-DNA complex has been shown in mice (Zhu et al., Science 261: 209–211, 1993). Moreover, safety studies in rodents and non-human primates of systemically administered cationic lipid-nucleic acid complexes have shown no significant toxicity associated with administering such complexes (Parker et al., Human Gene Therapy 6:575–590, 1995).

Cationic lipid-mediated transfection of mRNA in tissue culture was demonstrated to lead to translation of the transcript (Malone et al., Proc. Natl. Acad. Sci. 86:6077–6081, 1989). Delivery of antisense oligonucleotides to human endothelial cells using cationic lipids provided increased cellular uptake of the oligonucleotides and increased activity thereof in the cells (Bennett et al., Mol. Pharm. 41:1023–1033, 1992). The use of cationic lipids complexed to retroviral particles has allowed viral infection of cells which lacked the appropriate virus receptor (Innes et al., J. Virol. 64:957–962, 1990) or enhanced retroviral transduction using complexes known as virosomes (Hodgson et al., Nature Biotechnol. 14:339–342, 1996).

Immunotherapy for cancer using cationic lipid-nucleic acid complexes containing major histocompatibility (MHC)

genes directly injected into mice tumors elicited immune responses that resulted in tumor regression (Plautz et al., Proc. Natl. Acad. Sci. 90:4645–4649, 1993).

Human clinical studies are currently underway using cationic lipid-mediated delivery of DNA sequences encoding immunotherapeutic molecules in human melanoma, colorectal and renal cancer patients (Nabel et al., Proc. Natl. Acad. Sci. 90:11307–11311, 1993; Crystal, Science 270:404–410, 1995).

The cationic lipid formulations to date have often incorporated the phospholipid dioleoylphosphatidylethanolamine (DOPE). This phospholipid is thought to disrupt the endosomal membrane by destabilizing its bilayer structure, allowing the lipid-nucleic acid complex to escape endosomal degradation and to enter into the cytoplasm (Farhood et al., Biochem. Biophys. Acta 1235:289–295, 1995).

However, a significant obstacle in the widespread use of cationic lipid complexes for nucleic acid delivery to cells is the tendency of the complexes to form large aggregates in solution.

SUMMARY OF THE INVENTION

The present invention is directed to stable complexes or particles of cationic lipids and nucleic acid that can be used to deliver nucleic acid to a cell for the purpose of providing a therapeutic molecule to the cells of an individual in need of such treatment. The invention is also directed to stable complexes or particles of cationic lipids and nucleic acid which contain a stabilizing additive. The invention is further directed to methods for the preparation of homogenous suspensions of stable cationic lipid-nucleic acid complexes or particles by combining one or more cationic lipids, one or more colipids, one or more stabilizing additives and a nucleic acid or other ligand. The invention also includes a method for preparing an homogenous suspension of stable cationic lipid-nucleic acid complexes or particles using optionnally sizing procedures such as extrusion, which can also be used as the final sterilizing step in the production process of lipid-nucleic acid complexes for administration to patients for therapeutic purposes.

The invention is further directed to an homogenous suspension of stable lipid-nucleic acid complexes or particles produced by the above methods.

The invention may be understood with reference to the drawings of which the following is a brief description.

BRIEF DESCRIPTION OF THE DRAWINGS

FIG. 7 shows the effect of DSPE-PEG2000 on the in vitro transfection activity of lipid-DNA complexes in A549 cells as a function of plasmid DNA concentration. A) Expression level in the presence of 10 mol % DSPE-PEG2000 with respect to a buffer blank and B) in comparison to a preparation without DSPE-PEG2000.

DETAILED DESCRIPTION OF THE INVENTION

Figure 1:
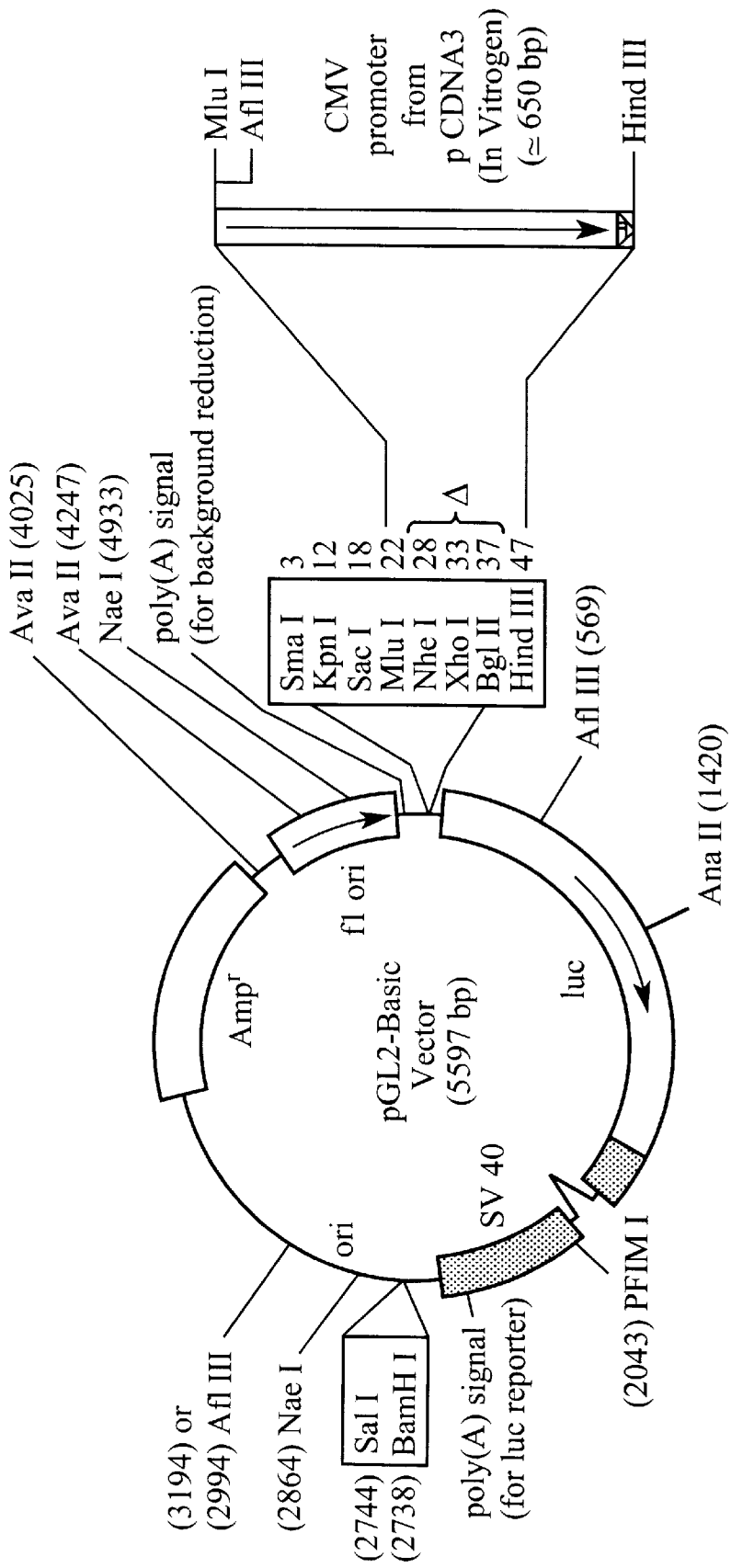
FIG. 1 shows a schematic diagram of plasmid pCMVluc.

The present invention is directed to stable complexes or particles of cationic lipids and nucleic acid that can be used to deliver nucleic acid to a cell for the purpose of providing a therapeutic molecule to the cells of an individual in need of such treatment. The invention is also directed to stable complexes or particles of cationic lipids and nucleic acid which contain a stabilizing additive. The invention is further directed to methods for the preparation of homogenous suspensions of stable cationic lipid-nucleic acid complexes by combining one or more or mixtures of cationic lipids, one or more colipids, one or more stabilizing additives and a nucleic acid or other ligand. The invention includes a method for preparing a homogenous suspension of stable nucleic acid complexes or particles, comprising combining one or more cationic lipids, one or more colipids, and one or more stabilizing additives to form a lipid suspension, combining the lipid suspension with a nucleic acid to form a complex or a particle, and optionnaly subjecting the complex or particle to a sizing procedure to form complexes or particles of homogenous size. The invention also includes a method for preparing an homogenous suspension of stable cationic lipid-nucleic acid complexes or particles using sizing procedures such as extrusion, which can also be used as the final sterilizing step in the production process of lipid-nucleic acid complexes for administration to patients for therapeutic purposes.

The complexes or particles of the invention include one or more cationic lipids, one or more colipids, one or more stabilizing additives, and a nucleic acid or other ligand.

The present invention is also directed to an homogenous suspension of stable lipid-nucleic acid complexes or particles, produced by:
 a) combining one or more cationic lipids, one or more colipids, and one or more stabilizing additives to form a lipid suspension,
 b) combining the lipid suspension with a nucleic acid to form a complex or a particle, and optionally
 c) subjecting the complex or particle to a sizing procedure.

The invention also includes the above homogenous suspension wherein the lipid suspension is further subjected to a sizing procedure such that a suspension of complexes or particles of homogenous size is produced.

"Stable complexes or particles" means that independently of their size said complexes or particles do not form aggregates.

"Homogenous suspension" is notably the result of a suspension containing non-aggregated complexes or particles.

According to the present invention homogenously sized complexes or particles may advantageously be obtained by an optionnal step subjecting said complexes or particles to a sizing procedure. Cationic lipids or mixtures of cationic lipids which may be used in the complexes of the invention include Lipofectin™ (a mixture of DOTMA (N-[1-(2,3-dioleoyloxy)propyl]-N,N,N-trimethylammonium chloride) and DOPE, 1:1 by weight), GIBCO-BRL; DDAB (dimethyl-dioctadecylammoniu-bromide); DMRIE (1,2-dimyristyl-oxypropyl-3-dimethyl-hydroxyethyl ammonium bromide); spermidine-cholesterol (spermidine-Chol); spermine-cholesterol (spermine-Chol); DC-chol (3β[N-(N', N'-dimethylaminoethane)-carbamoyl] cholesterol); Transfectam™ (DOGS, dioctadecylamidoglycylspermine), Promega; DOSPER (1,3-di-oleoyloxy- 2-(6-carboxy-spermyl)-propylamide), Boehringer Mannheim; DOTAP (N-[1-(2,3-dioleoyloxy)propyl]-N,N,N,-trimethyl-ammoniummethylsulfate), Boehringer Mannheim; Tfx™ 50 (a mixture of N,N,N',N',-tetramethyl-N,N',-bis (2-hydroxyethyl)-2,3-dileoyloxy-1,4-butamediammonium iodide and DOPE), Promega; Lipofectaminetm (DOSPA), Lipofectace™ (a mixture of DDAB and DOPE, 1:2.5 by weight), GIBCO-BRL.

Preferably, the cationic lipids of the present invention are selected from among spermidine-cholesterol, spermine-cholesterol, DC-chol, and DOGS. Most preferably, the cationic lipid is any of the isomers of spermidine-cholesterol.

Colipids are added to the complexes in order to facilitate entry of the nucleic acid into the cell or to conjugate additives that increase stability. Colipids of the invention include neutral, zwitterionic, and anionic lipids.

A preferred colipid which may be added to the complexes in order to facilitate entry of the complexes into the cell is dioleoylphosphatidylethanolamine (DOPE).

In a preferred embodiment, the colipid DOPE is complexed to the cationic lipid in order to facilitate transport of the complex across the cell membrane and prevent endosomal degradation.

The ratios of cationic lipid to colipid (on a weight to weight basis) can range from 1:0 to 1:10. In preferred embodiments, the ratio ranges from 1:0.5 to 1:4.

Other colipids may also be added to the complexes of the invention to allow the attachment of stabilizing additives to the complex. The colipid can be a moiety that allows the stabilizing additive to be incorporated into the complex of the invention. Derivatization of the lipid with an additive allows the moiety to anchor the stabilizing additive to the cationic lipid complex. The colipid can be conjugated to additives which prevent aggregation and precipitation of cationic lipid-nucleic acid complexes.

Colipids which may be used to incorporate such additives to the cationic lipid-DNA complexes of the invention include, but are not limited to, zwitterionic or other phospholipids. Preferably, the colipid used to conjugate a stabilizing additive is a moiety capable of being incorporated into the complexes of the invention. More preferably, such a colipid is inert and biocompatible.

In a preferred embodiment, the phospholipid distearoylphosphatidylethanolamine (DSPE) is derivatized with a stabilizing additive and is the moiety capable of being incorporated into the cationic lipid-nucleic acid complexes of the invention.

In another embodiment of the invention, cationic lipids may be synthesized to contain stabilizing additives such as polyethylene glycol (PEG), which product would bind to nucleic acid in a complex of the invention through electrostatic interactions.

Stabilizing additives can also be added to the complexes of the invention to maintain the integrity of the complexes, to maintain complex stability during sizing procedures, and to increase shelf life. The additives are preferably bound to a moiety capable of being incorporated into or binding to the complex, for example, a colipid. Such additives generally are selected from among hydrophilic polymers, which include, but are not limited to, polyethylene glycol, polyvinylpyrrolidine, polymethyloxazoline, polyethyloxazoline, polyhydroxypropyl methacrylamide, polylactic acid, polyglycolic acid, and derivatized celluloses such as hydroxymethylcellulose or hydroxyethylcellulose (PCT Publication No. WO94/22429, published Oct. 13, 1994). Other stabilizing additives useful in the present invention include perfluorinated or partially fluorinated alkyl chains, fluorinated phospholipids, fatty acids and perfluoroalkylated phospholipids and polyglucoronic acids (Oku et al., Critical Reviews in Therapeutic Drug Carrier Systems 11:231–270, 1994).

Preferably, the phospholipid DSPE is derivatized with polyethylene glycol (PEG) to form the stabilizing additive DSPE-PEG. More preferably, the molecular weight of PEG that may be used ranges from 300 to 20,000 Da. In a still more preferred embodiment, PEG2000 is used as the stabilizing additive.

The PEG-lipid conjugate can be prepared by several methods, including use of the linker cyanure chloride (U.S. Pat. No. 5,225,212, incorporated herein by reference). Other activating methods can be used, including those which use carbonyldiimidazole (C=O), succinic anhydride (—CO—CH$_2$—CH$_2$—CO—), or tosylate:

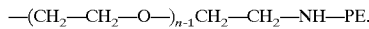

A proposed general structure of additives is as follows (PE=phosphatidylethanolamine):
Where the polymer is polyethylene glycol:

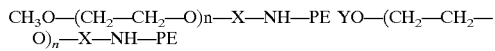

Average molecular weight: 300–10000 Da, (n=5–250)
X: linker (CO; cyanure chloride, see U.S. Pat. No. 5,225,212)
Y: ligand (peptide, carbohydrate, protein, digionucleotide, vitamin, receptor antagonist or agonist, . . . )

In another embodiment of the invention, a ligand may be coupled to the stabilizer or PEG moiety of a complex of the invention using a free —OH group. Such ligands include, but are not limited to peptides, carbohydrates, proteins, nucleic acids, vitamins, receptor antagonists and receptor agonists. Where the ligand is a digionucleotide, a PEG-digionucleotide conjugate may be prepared. Methods to activate the —OH group for coupling of the ligand include those which use carbonyldiimidazole, cyanure chloride, succinic anhydride or tosylate. Preferably, the ligand contains a free NH2 or SH group available for coupling.

An example is the following:

The coupling of the ligand may be done at any of several stages of complex formation, including at the molecular level between DSPE-PEG-OH and the ligand, at the level of the lipid suspension, or at the level of the lipid-DNA complex. Preferably, the coupling is performed at a later stage of complex formation, with an increased probability that the ligand will be on the surface of the complex and therefore accessible.

Stabilizing additives which allow for increased storage of the cationic lipid-nucleic acid complexes may be added to the complexes so as to achieve such long-term stability, but must be added so that the additives do not interfere with the binding of the nucleic acid to the cationic lipid, especially at lower charge ratios. The molar ratio of a stabilizer additive, such as a derivatized phospholipid, to the colipid (for example, DSPE-PEG2000/DOPE) may range from 0.01 to 1 (0.5 mol % to 50 mol % with respect to the total lipid amount). In a preferred embodiment, the stabilizer additive may be added into the mixture of cationic lipid and colipid at concentrations of from 1 to 20 mol % of total lipid. In a more preferred embodiment, the molar ratio of stabilizer additive to colipid may range from 0.04 to 0.2.

The complexes of the present invention also include a desired nucleic acid component which is to be delivered to a cell in need of such a molecule. The nucleic acid which is complexed with the lipid suspension or cationic lipid may be a DNA or RNA molecule, which may be single or double stranded. The nucleic acid may be, inter alia, a genomic DNA, a cDNA, an mRNA, an antisense RNA, or a ribozyme. The nucleic acid may also be in the form of a plasmid or linear nucleic acid which contains an expressible sequence of nucleic acid that can generate a protein, ribozyme, antisense, or other molecule of interest upon delivery to a cell. The nucleic acid can also be an oligonucleotide which is to be delivered to the cell, e.g., for antisense or ribozyme functions. In a preferred embodiment using expressible nucleic acid, plasmid DNA is used. Concentrations of nucleic acid which may be added to the cationic lipids or lipid suspensions to form the complexes of the invention range from 10 μg/ml to 1000 μg/ml. In a preferred embodiment of the invention, the concentration of nucleic acid ranges from 20 μg/ml to 500 μg/ml.

The cationic lipid-nucleic acid complexes of the invention may also be characterized by their charge ratio (+/−), which is the ratio of the positively charged cationic lipid component to the negatively charged nucleic acid component of the complex. In general, an excess positive charge on the complex facilitates binding of the complex to the negatively charged cell surface. The charge ratio of a complex of the invention may be calculated by dividing the sum of the positive charges by the negative charges on the complex. A determination of the positive charge per mole can be made for a specific cationic lipid or colipid such that a given weight of lipid will represent a specific positive charge. An analogous determination can be made with respect to the nucleic acid or colipid to yield the negative charge per mole so that a given weight of nucleic acid or colipid will represent a specific negative charge. By dividing all positive charges by all negative charges, the net charge ratio (+/−) of the complex is determined.

Preferably, the range of the charge ratio of the complexes of the invention are from 1 to 20 (+/−). More preferably, the range is from 2.5 to 10 (+/−).

The invention is also directed to methods for homogenous sizing of the lipid suspensions (before addition of nucleic acid) and/or lipid-nucleic acid complexes using sizing methods which standardize the particle size of the lipid suspensions or lipid-nucleic acid complexes. Extrusion before the addition of nucleic acid would reduce nucleic acid binding to lipid aggregates. Methods which can be used to produce homogenous preparations or suspensions of the complexes include, but are not limited to, extrusion, sonication and microfluidization, size exclusion chromatography, field flow fractionation, electrophoresis and ultracentrifugation.

In a preferred embodiment of the invention, a method comprising extrusion of lipid suspensions or/and lipid-nucleic acid complexes through membranes of defined pore diameter is used to prepare homogenously sized particles or preparations of the complexes of the invention without modification of the complexed nucleic acid. An extruder may be used in which polycarbonate membranes of defined pore diameter are stacked so that the suspension is forced through the membranes under pressure (for example, from Lipex Biomembranes, Inc., Vancouver, Canada). Lipid suspensions or/and cationic lipid-nucleic acid complexes may be extruded through membranes having pores of 50 to 500 nm diameter. Preferred membranes have a pore diameter of 200 nm. Extrusion of the complexes can also be used as the final sterilizing step in the production process of cationic lipid-nucleic acid complexes for administration to patients for therapeutic purposes.

In a preferred embodiment of the invention, the particle size of a cationic lipid-nucleic acid complex may range from 25 to 500 nm. More preferably, the particle size of a complex is 200 nm. Particle size may be selected for optimal use in a particular application. For example, where a particular clinical application involves extravasation of the cationic lipid-nucleic acid complexes, the complex size may be about 80 nm or lower.

Measurements of particle size can be made by a number of techniques including, but not limited to, dynamic laser light scattering (photon correlation spectroscopy, PCS), as well as other techniques known to those skilled in the art (see Washington, Particle Size Analysis in Pharmaceutics and other Industries, Ellis Horwood, New York, 1992, pp. 135–169).

After the complexes of the invention have been subjected to a sizing procedure, e.g., extrusion, the yield percentage may be calculated to assess the recovery. This calculation is based on determining the concentration of nucleic acid in the complexes before and after the procedure. For example, where a suspension of complexes containing DNA is extruded through sizing membranes, the DNA concentration in the suspension may be determined using standard techniques, e.g., measurement of absorbance at 260 nm (A260), which detects nucleic acid. The presence of 10% DMSO facilitates the determination of DNA concentration in the presence of lipid. The yield percentage after extrusion may be calculated from the ratio of the DNA concentrations determined before and after extrusion.

To determine the structural integrity of the nucleic acid in the complexes following a sizing procedure, the nucleic acid may be analyzed, for example, by agarose gel electrophoresis after solvent extraction of the lipids. The use of restriction mapping of the nucleic acid may provide additional detail regarding the state of a plasmid, for example. Using such techniques, it is possible to determine whether the nucleic acid in a complex remains structurally intact and is not degraded by shear forces during pressurized filtration or other mechanical stresses generated in sizing procedures.

It is also possible to assess the structural stability of the complexes in terms of how tightly the DNA is bound and covered by the lipid or lipid stabilizer component of the complex. This may be measured by assessing DNA migration in an agarose gel (no migration indicates that the DNA is covered with the lipid) or by incubation with DNAseI followed by lipid extraction and agarose gel electrophoresis to assess whether the DNA in the complex was exposed to the surface.

The complexes of the invention may be stored at 4° C. for optimal stability. Stability of the complexes over time may be determined by periodic assessment of particle size, using methods previously described for such measurement.

The cationic lipid-nucleic acid complexes are also useful for transfer of nucleic acid into cells for the purpose of monitoring behavior of the nucleic acid in the cell environment. For example, cationic lipid transfection of a gene into cells of interest may be used to determine regulatory parameters that allow expression of the gene-enhancers, promoters, etc.- by linking these elements to the gene of interest and assaying for expression.

The cationic lipid-nucleic acid complexes can be used for delivery of the nucleic acid to the cells of an individual in need of treatment by such molecules. Routes of administration include, but are not limited to direct injection (e.g., intratracheal), aerosolization, intramuscular, intra-tumoral and intravenous routes for in vivo administration. Cationic-lipid-mediated transfection of nucleic acid into cells used in ex vivo transplantation procedures can also be used to deliver nucleic acid to an individual in need of such molecules.

Therapeutic transgenes that can be used as the nucleic acid component of the complexes of the invention include, but are not limited to, CFTR for cystic fibrosis, α1-antitrypsin for emphysema, soluble CD4 for AIDS, ADA for adenosine deaminase deficiency, dystrophin for muscular dystrophy, cytokine genes for cancer treatment, immunotherapeutic or tumor suppressor genes for cancer treatment, and any other genes that are recognized in the art as being useful for gene therapy. The nucleic acid component may also include mRNA. Transgenic nucleic acids encoding molecules such as ribozymes, antisense RNA, or oligonucleotides can also be contained in the nucleic acid component of a complex of the invention. Alternatively, ribozymes, antisense nucleic acid or oligonucleotides may be directly incorporated into the complexes of the invention. The nucleic acid constructs may also contain regulatory elements that govern expression of the gene, such as enhancers and promoters.

Where complexes comprising an expressible nucleic acid are delivered to a wide variety of cell types, e.g., by various administration routes including intravenous administration, leading to systemic uptake of the lipid-nucleic acid complexes, expression of the nucleic acid may be limited to specific tissues by the use of tissue-specific promoters. Temporal control of expression of nucleic acid also may be achieved with the use of inducible promoters that are activated in response to an exogenous stimulus, e.g., an MMTV promoter activated by metallothionin, a TAR/RRE comprising promoter activated in the presence of the TAT/REV proteins of HIV, or a hormone responsive promoter.

Where the nucleic acid component of the complex comprises an expressible gene, the biological function thereof may be assayed by standard techniques, including detection of mRNA by Northern blot or SI analysis, and/or detection of protein using Western blotting, immunoprecipitation or functional protein assay. The latter is particularly useful where a gene encodes a suitable marker protein, e.g., luciferase or P-galactosidase.

The cationic lipid-nucleic acid complexes may transfer the nucleic acid of interest to cells in vitro for the purpose of determining the function of such nucleic acid, or for the purpose of providing such cells with a nucleic acid that provides a therapeutic benefit, or for the purpose of determining the efficiency and specificity of the complexes for nucleic acid delivery. Such cells may include, but are not limited to, established cell lines, e.g., A549, NIH3T3, HeLa, as well as primary cells or other cells known to those skilled in the art.

The nucleic acid of interest may also be delivered in vivo to cells of an animal model which can be used to determine the efficiency and specificity of transfer to the tissues of a whole organism. Such animals include mice (e.g., C57 Black/10 or Balb/c), rabbits, and primates as well as others. Animal models of human disease states may be used to test the efficacy of certain molecules for therapeutic treatment, e.g., transgenic mice engineered to express a mutant CFTR gene as a model of cystic fibrosis.

The present invention also encompasses pharmaceutical compositions containing the complexes of the invention which can be administered in a therapeutically effective amount to deliver a desired nucleic acid to an individual needing therapy. The pharmaceutical compositions can include pharmaceutically acceptable carriers, including any relevant solvents. As used herein, "pharmaceutically acceptable carrier" includes any and all solvents, dispersion media, coatings, antibacterial and antifungal agents, isotonic and absorption delaying agents, and the like. Except insofar as any conventional media or agent is incompatible with the active ingredient, its use in the therapeutic compositions is contemplated.

The practice of the invention employs, unless otherwise indicated, conventional techniques of recombinant DNA technology, protein chemistry, microbiology and virology which are within the skill of the art. Such techniques are explained fully in the literature. See, e.g., Current Protocols in Molecular Biology, Ausubel et al., eds., John Wiley & Sons, Inc., New York, 1995.

The invention is illustrated by reference to the following examples.

EXAMPLE 1

Preparation of Cationic Lipid-Nucleic Acid Complexes

Cationic lipids DC-Chol (3β[N-(N',N'-dimethyl-aminoethane)-carbamoyl] cholesterol) (synthesized according to Gao, X. and Huang, L., Biochem. Biophys. Res. Communic. 179:280–285, 1991); spermidine-cholesterol (spermidine-Chol) (synthesized at Transgene, S. A.) (Caffey et al., J. Biol. Chem. 270:31391–31396, 1995; French Application No. 96 01347, both incorporated herein by reference) spermine-cholesterol (spermine-Chol) (synthesized at Transgene, S. A.) (Caffey et al., J. Biol. Chem. 270:31391–31396, 1995; French Application No. 96 01347) and diocta-decylamido-glycyl-spermine (DOGS) (generous gift of Dr. Jean-Paul Behr (Behr et al., Proc. Natl. Acad. Sci. 86:6982–6986, 1989, incorporated herein by reference), and colipids dioleoylphosphatidylethanolamine (DOPE) (Sigma, Ref. P5058, lot 75H8377) and distearoyl-phosphatidyl-ethanolamine-PEG2000 (DSPE-PEG2000, Avanti Polar Lipids, Alabaster, Ala., USA, Ref 880120, lot 18OPEG2PE-21) were combined at the required ratios (ratios of cationic lipid:DOPE of 1:1; ratio of DSPE-PEG2000 to total lipid of 2, 5 and 10 molt) by mixing the respective solutions in chloroform/ethanol (8:2) and evaporating the solvents under a stream of nitrogen to produce a dried lipid film. Residual solvents were evaporated under vacuum. The dried lipid film was rehydrated at 4° C. overnight with slight agitation in 20 mM Hepes, pH 7.8, 0.9% NaCl and suspended by sonication for 8 min in a bath sonifier (Bransonic 221).

The cationic lipid/colipid mixtures were extruded at 200 nm before complexing them with DNA at different charge ratios +/−. Extrusion was performed using an extruder from Lipex Biomembranes, Inc. (Vancouver, Canada) equipped with a stack of 2 polycarbonate membranes having pores of 0.2 µm diameter (Nucleopore, Costar Corp. Cambridge, Mass., USA). The suspension was forced through the membranes under nitrogen gas pressure of approximately 10 bar at 50° C.

In a particular example, the following lipids were mixed and dried: 422 µl of Spermidine-Chol (10 mg/ml), 422 µl DOPE (10 mg/ml) and 145 µl DSPE-PEG2000 (25 mg/ml) under a stream of nitrogen, followed by evaporation of residual solvent under vacuum. Reconstitution was achieved by adding 4.32 ml 20 mM Hepes, pH 7.8+0.9% NaCl overnight at 4° C. on a shaker, followed by sonication in a bath sonifier (Bransonic 221) for 8 min to give the following lipid concentrations: spermidine-Chol: 1.75 mM, DOPE: 1.31 mM, DSPE-PEG: 0.31 m-M. The lipid suspension was extruded through a stack of 2 membranes of 200 nm pore diameter. The suspension was forced through the membranes under nitrogen gas pressure of approximately 10 bar at 50° C. 200 µl pCMVluc plasmid DNA was added (1.46 mg/ml in 10 mM Tris-HCl, pH 7.5, 1 mM EDTA) to an aliquot of 1.26 ml of the lipid suspension to reach a final volume of 1.46 ml. The concentrations of the components in the final preparation of the complex were: spermidine-Chol: 1.51 mM; DOPE: 1.13 mM; DSPE-PEG: 0.27 mM; DNA: 200 µg/ml. Such a complex contains 10 mol % DSPE-PEG2000 and has a charge ratio of 5 at a DNA concentration of 200 µg/mi.

The lipid-DNA complexes were again extended through a 200 nm pore diameter polycarbonate membrane at 50° C. and approximately 10 bar nitrogen pressure. See FIG. 4 for comparison of the stability of extruded and non-extruded lipid-DNA complexes.

The plasmid containing the luciferase gene under the control of the CMV promoter, pCMVluc is shown in FIG. 1.

The particle size of the cationic lipid-nucleic acid complexes that were obtained was determined by photon correlation spectroscopy (also called dynamic light scattering), a technique which is based or laser light scattering. PCS measures the Brownian movement of particles in the illuminated volume of the laser beam and calculates a correlation function which links the fluctuations in scattered light to the diffusion coefficient of the particles. The particle size is then derived from the diffusion coefficient using the Stokes-Einstein relationship: $D=kT/3\pi\eta d$ (k: Boltzmann constant; T: absolute temperature; η: viscosity; d: particle diameter (see Clive Washington, Particle Size Analysis in Pharmaceutics and other Industries, Ellis Horwood publisher, New York, 1992, pp 135–169; contains also chapters on other methods).

PCS was performed on an aliquot before extrusion, while the remainder was extruded through a 200 nm membrane at 50° C. Particle diameter was again determined by PCS after extrusion. The cationic lipid-nucleic acid complexes were stored at 4° C. for various time periods to determine their stability.

The concentration of DNA in the cationic lipid-nucleic acid preparations was determined by clarifying the lipid suspension with 10% (v/v) dimethylsulfoxide (DMSO). Absorbance was measured at 260 nm using the relationship that defines 50 µg/ml DNA as equal to 1 absorbance unit at a path length of 1 cm. Measurements were performed before and after extrusion for the different preparations and compared with the concentration of non-complexed plasmid DNA. The yield percentage is calculated by taking the ratio A260 (after extrusion)/A260 (before extrusion) (×130).

The physical integrity of DNA in the complexes was determined by agarose gel electrophoresis after solvent extraction of the lipids. To this end, 1 ml of cationic lipid-nucleic acid suspension was mixed with 0.4 ml water, 2 ml methanol and 1 ml chloroform and vortexed for 2 min. After centrifugation for 5 min at 3,000 rpm the upper phase was transferred to a separate tube and dried under vacuum. The pellet was redissolved in 250 pi of water to which 27 µl 3M sodium acetate and 5 µg transfer RNA were added, followed by the addition of 700 µl absolute ethanol that had been cooled to −20° C. After brief vortexing and 1 h at −20° C., the DNA pellet was recovered by centrifugation at 15,000 rpm for 30 min at 4° C. The liquid was decanted and the remaining pellet was washed twice with 200 µl of 70% aqueous ethanol (cooled to −20° C.) and recovered by centrifugation after each wash. The pellet was then dried under vacuum and redissolved in 10 mM Tris-HCl, pH 7.5, 1 mM EDTA to an approximate final concentration of 0.5 µg/pl. Agarose gel electrophoresis was performed in submarine slab gels (14×10×0.8 cm) in 1% agarose (Sigma, Ref. A-6877, lot 123HO552) in Tris (4.86 g), sodium acetatex3 H20(0.68 g) and EDTA (0.336 g, all weights are for 1 liter final volume, adjusted to pH 7.8 with acetic acid) at 60 volts for 2 h. DNA bands were stained with ethidium bromide in the above buffer at 60 µg/l.

Particle size analysis was performed by laser light scattering (10 mW He—Ne laser at 632.8 nm) combined with PCS (Coulter N4 Plus, Miami, Fla., USA) over the range of 3–10,000 nm. Scattered light was measured at an angle of 90° of the sample diluted in 20 mM Hepes, pH 7.8, 0.9% NaCl to obtain between $5\times10^4$ and $10^6$ counts/sec. The final volume was 500 µl. The measurement was started after 3 min equilibration at 25° C. using the following parameters: automatic prescale; sample time: automatic; run time automatic (3 min at 900); SDP (algorithm to discriminate between different populations) analysis from 3 to 10,000 nm using 25 bins; refractive index: 1.33252; viscosity: 0.8904 centipoise.

After a first analysis performed under the above conditions, the measurement conditions were refined by reducing the size of the window and by increasing the number of bins. The system was calibrated with latex beads of defined average particle diameter (Coulter size controls: CEI NO. 6602336; 90, 170, 300 and 500 nm). Adjustment of the delay time was done automatically and was regularly verified to be in the correct range by manual measurements on the calibrated beads.

Results

Figure 2:
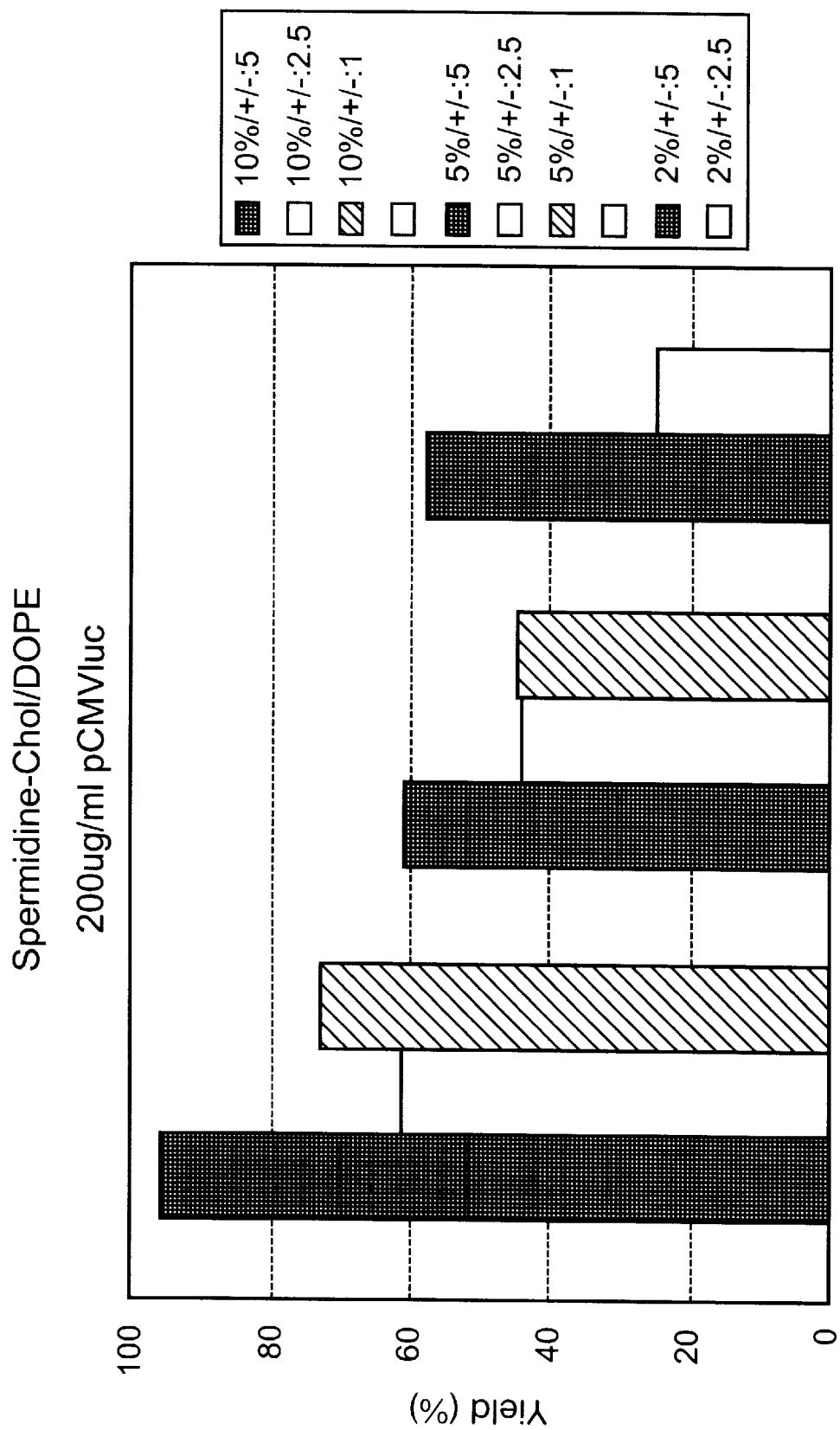
FIG. 2 shows recovery of plasmid DNA after extrusion of DNA vector complexes containing spermidine-Chol/DOPE complexed to 200 µg/ml DNA through a 200 nm pore size. Percent yield is shown as a function of the molar percentage of distearoylphosphatidyl-ethanolamine-polyethylene glycol (DSPE-PEG) and the charge ratio (+/−) of the complex.
Figure 3:
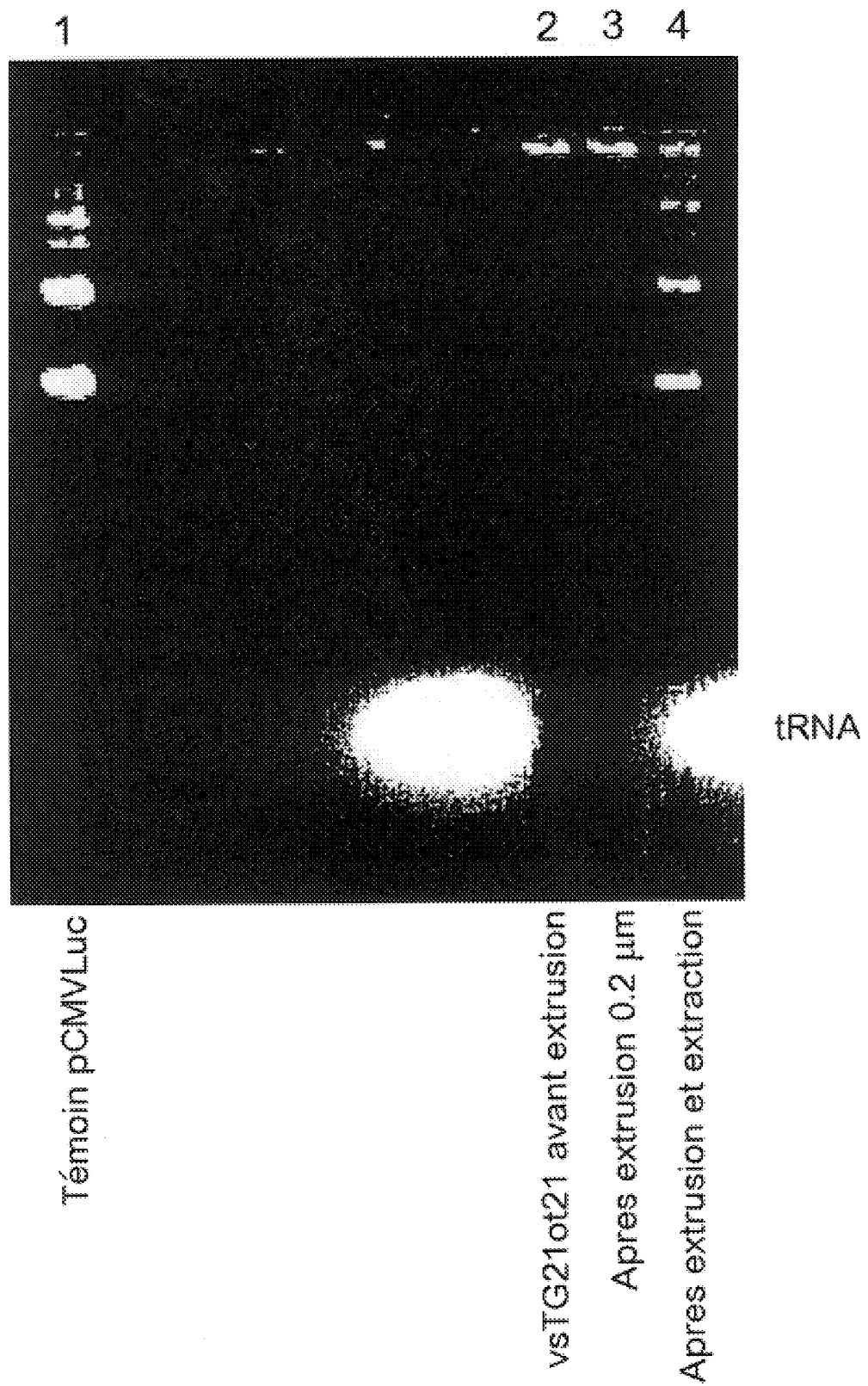
FIG. 3 shows the integrity of pCMVluc plasmid DNA after extrusion of lipid-DNA complexes at 200 nm pore diameter determined by agarose gel electrophoresis (lane 1: pCMVluc; lane 2: pCMVluc before extrusion of complexes containing 200 µg/ml plasmid DNA complexed to Spermidine-Chol/DOPE (1:1 by weight) and 2 mol % DSPE-PEG2000 at a charge ratio +/−=5; lane 3: pCMVluc plasmid DNA in the same preparation after extrusion at 0.2 µm; lane 4: the same preparation as shown in lane 3 followed by extraction of the lipids to isolate the completed DNA). The spot at the bottom of the gel corresponds to carrier tRNA which is used to coprecipitate the plasmid DNA.
Figure 4A:
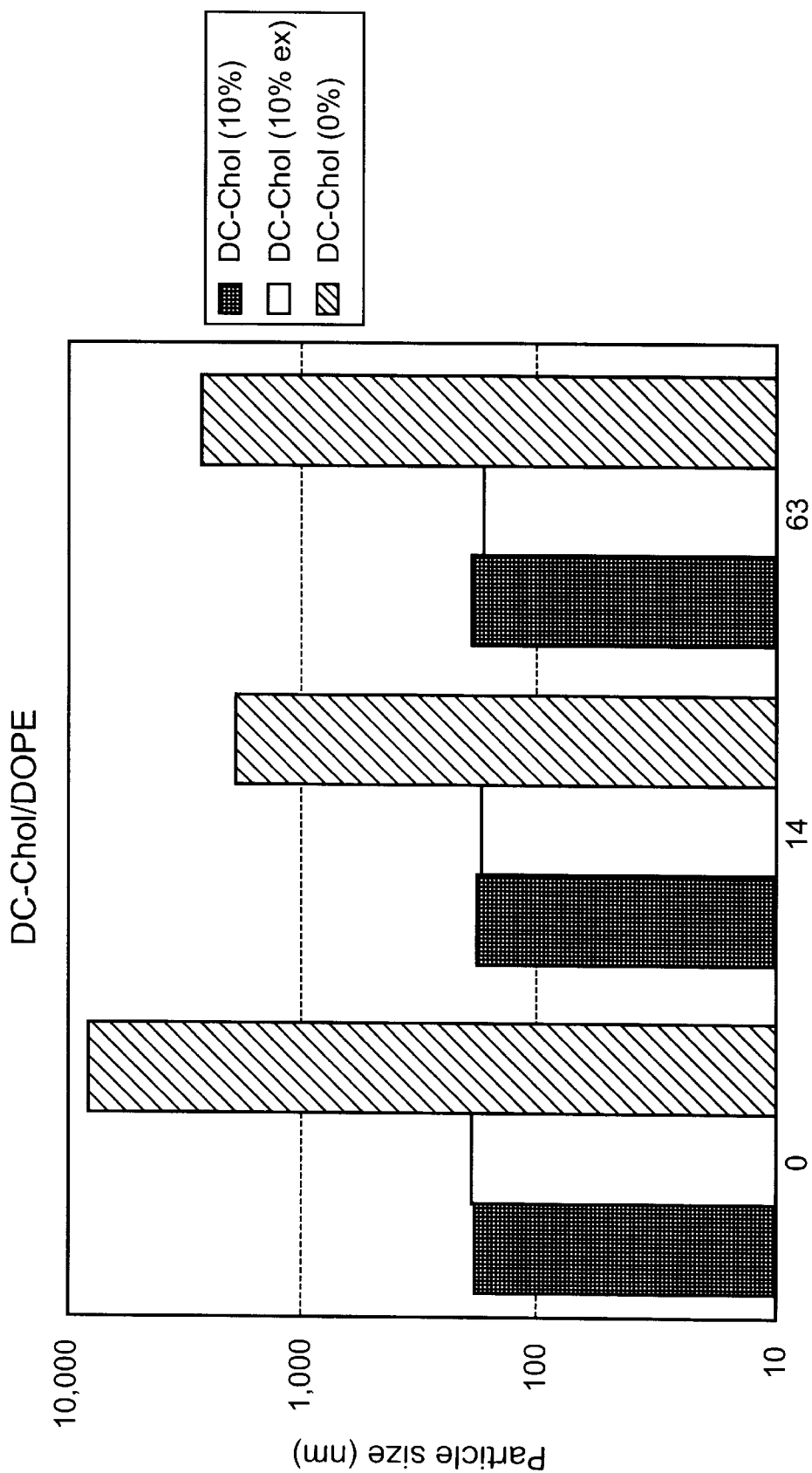
FIGS. 4(A–D) shows the effect of the molar percentage of DSPE-PEG2000 on the stability of lipid-DNA complexes at 4° C. for different cationic lipids at 20 µg/ml DNA concentration as a function of time, as measured by photon correlation spectroscopy after or without extrusion step. Black columns show the size of different DNA-cationic lipids complexes containing 10% of DSPE-PEG2000 prepared without extrusion step; white columns show the size of different DNA-cationic lipids complexes containing 10% of DSPE-PEG2000 after extrusion; and grey columns show the size of different DNA-cationic lipids, complexes containing 0% of DSPE-PEG2000 and prepared without extrusion step. A: DC-Chol/DOPE; B: Spermidine-Chol/DOPE; C: Spermine-Chol/DOPE; D: DOGS/DOPE.
Figure 4B:
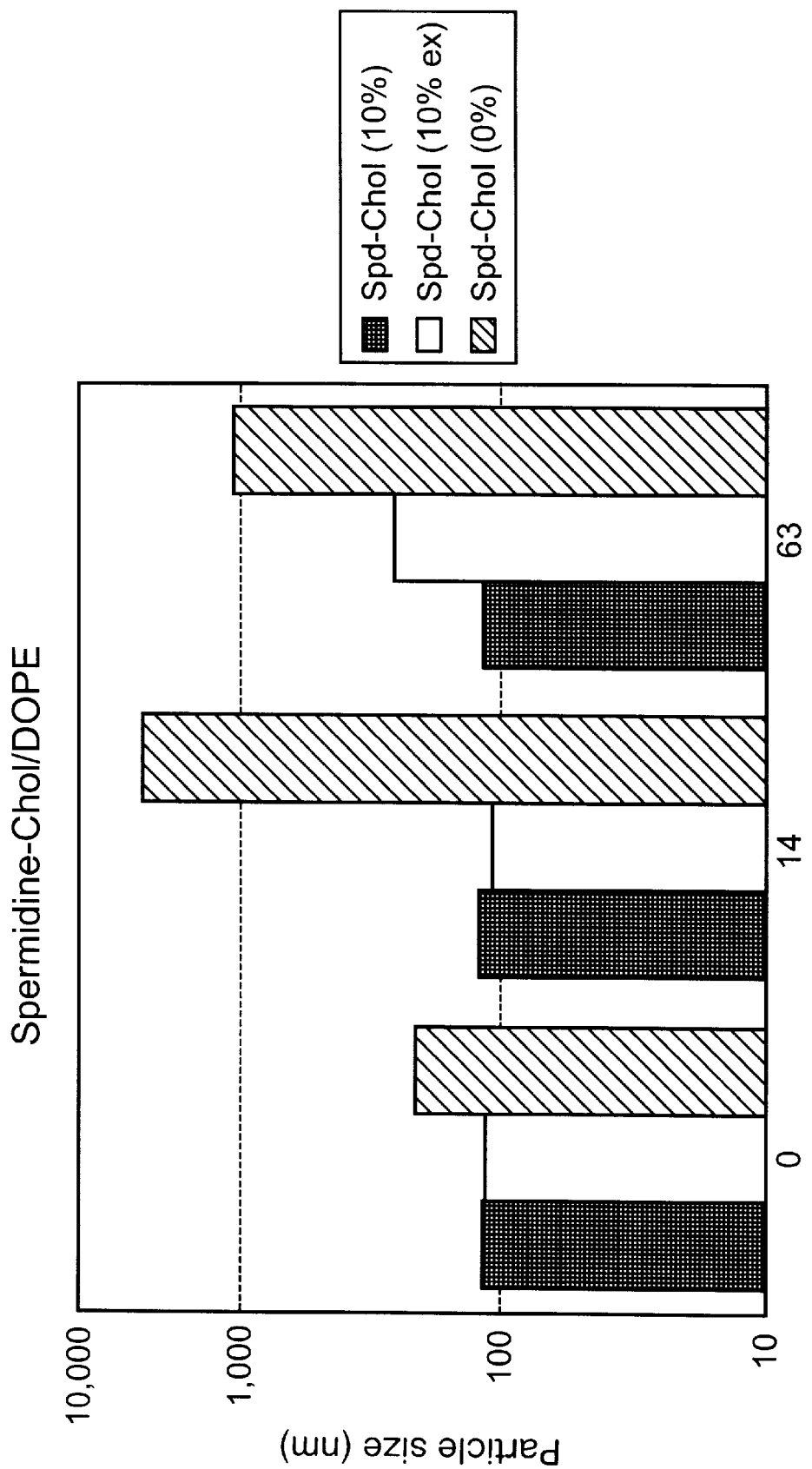
Figure 4C:
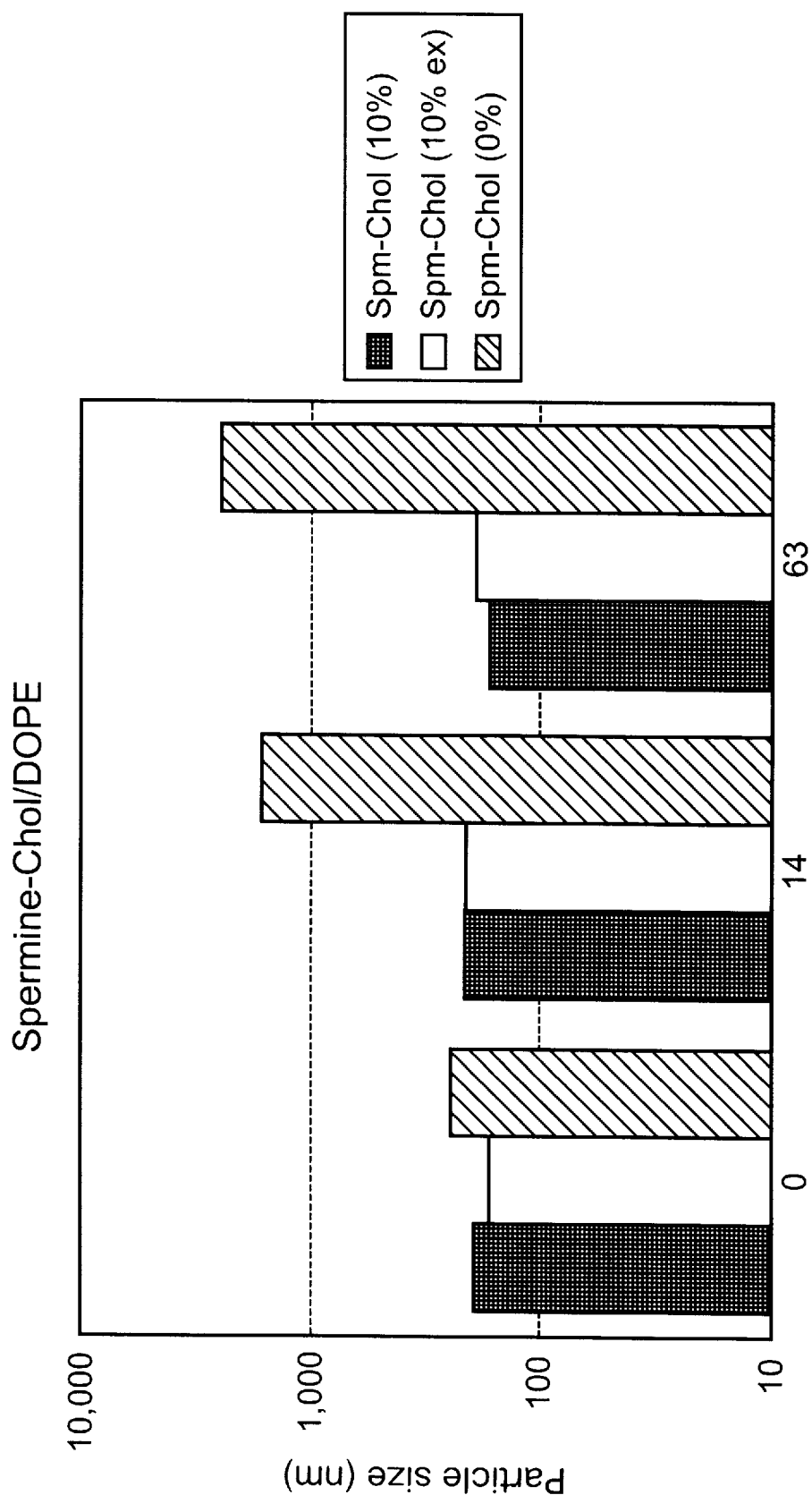
Figure 4D:
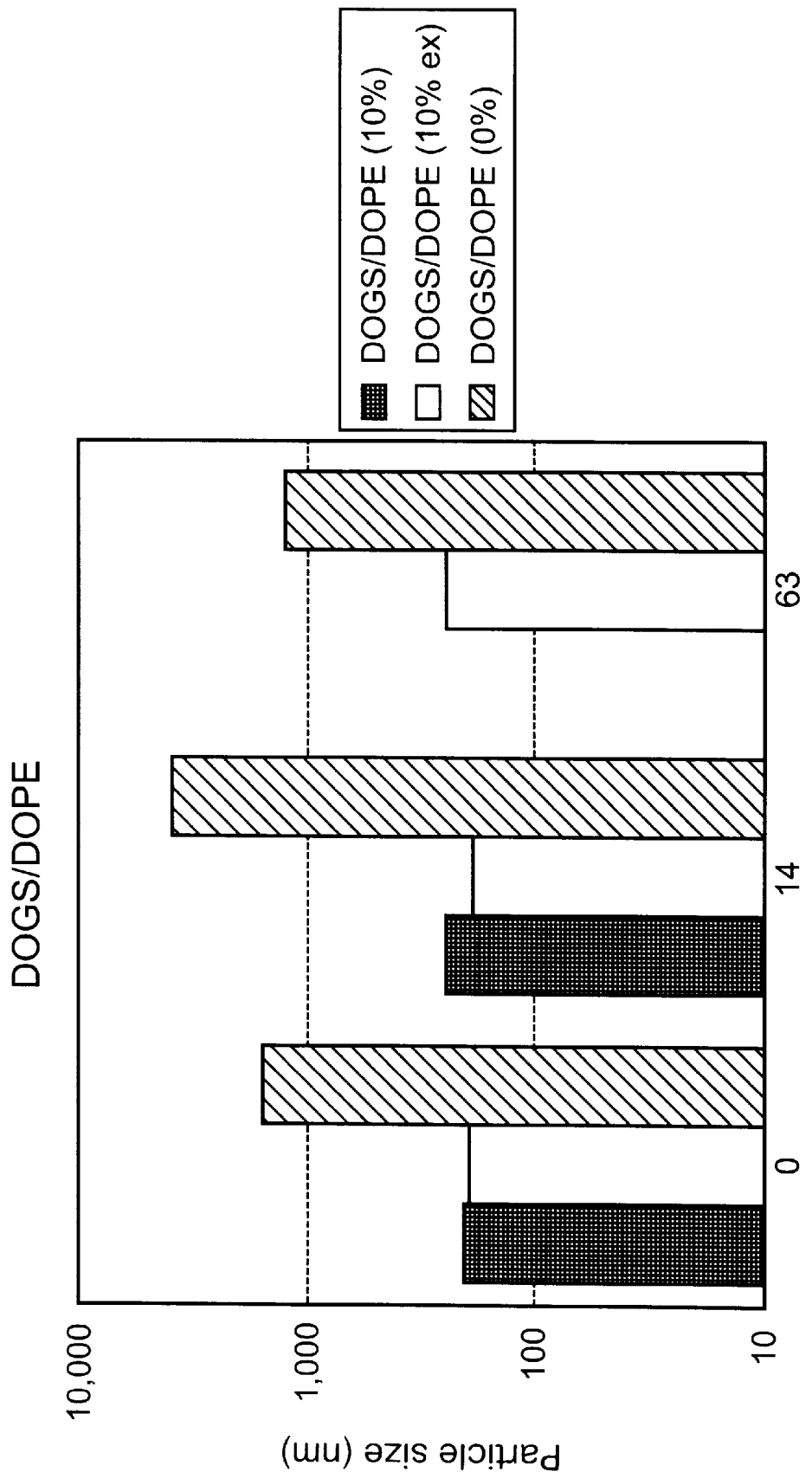

Incorporation of PEG-phospholipids (PEG-PL) such as distearoylphosphatidylethanolamine coupled to PEG2000 (DSPE-PEG) at molar ratios of 10% significantly improved DNA recovery after extrusion while maintaining its integrity by preventing aggregation (FIGS. 2 and 3). This beneficial effect was already apparent upon visual inspection of the obtained complexes which were homogenous dispersions in the case of added PEG-PLs but became rapidly flocculent if the stabilizer additive was omitted. Initial attempts to extrude lipid-nucleic acid complexes which contained no stabilizing additives through polycarbonate membranes with a pore diameter of 200 nm had shown that most of the DNA was lost on the filter membrane most likely because of the presence of aggregates.

Stability studies using various cationic lipids complexed to 20 µg/ml plasmid DNA at 4° C. showed that the average particle diameter of the complexes as determined by PCS remained stable for at least 2 months (FIGS. 4A–D; A: DC-Chol/DOPE; B: Spermidine-Chol/DOPE; C: Spermine-Chol/DOPE; D: DOGS/DOPE). Initial particle size is shown at day 0, and the particle size was measured over a 63 day period, as a function of the mol % of DSPE-PEG 2000 and whether extrusion of the DNA-lipid complexes was performed ("ex") The data shows that the addition of 10% DSPE-PEG maintained the particles at uniform size, preventing aggregation, in contrast to the preparations without DSPE-PEG (0%).

Figure 5:
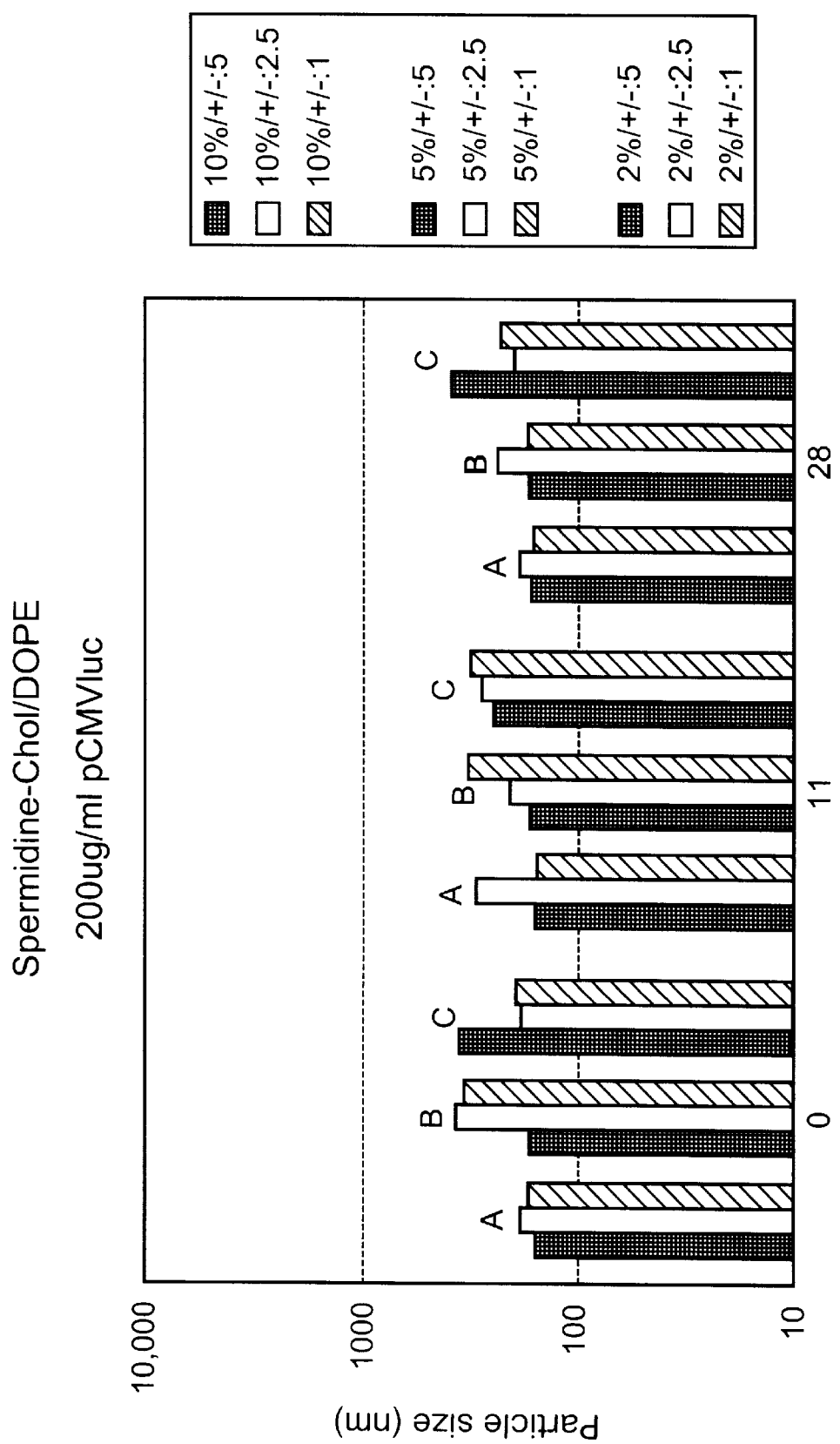
FIG. 5 shows the effect of different concentrations of DSPE-PEG2000 and of different +/− charge ratios on the stability of lipid-DNA complexes containing spermidine-Chol/DOPE at a 200 µg/ml DNA concentration after extrusion as a function of time. Black columns show +/−:5 charge ratios effect; white columns show +/−:2,5 charge ratios effect; and grey columns show +/−:1 charge ratios effect. A: 10% DSPE-PEG2000, B: 5% DSPE-PEG2000, C: 2% DSPE-PEG2000.

The stabilizing effect of DSPE-PEG was also observed for lipid-DNA complexes containing spermidine-Chol/DOPE complexed to higher plasmid DNA concentrations (200 µg/ml) that are necessary for in vivo transfections (FIG. 5). The results show that the stabilizing effect of DSPE-PEG2000 is observed for different amounts of the additive (2, 5 and 10 mol %) as well as for different +/− charge ratios. Minor fluctuations in the measured size by PCS do not indicate instabilities of the preparations, since they do not evolve with time. It is more likely that size estimations by PCS may have introduced theses fluctuations, possibly due to slight changes in the shape of the complexes.

Figure 6:
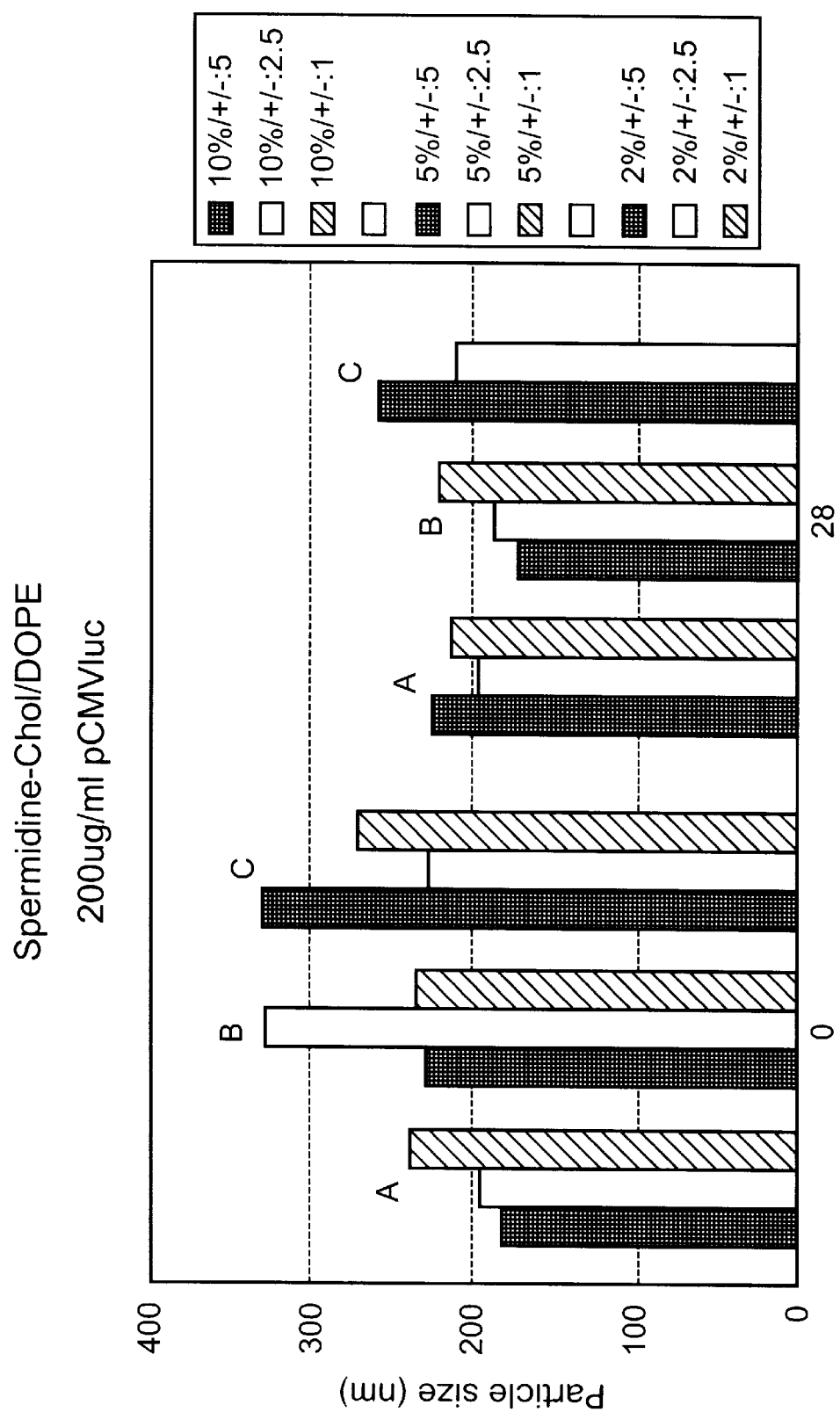
FIG. 6 shows the effect of different concentrations of DSPE-PEG2000 and of different +/− charge ratios on the stability of lipid-DNA complexes containing spermidine-Chol/DOPE at a 200 µg/ml DNA concentration before extrusion as a function of time. Black columns show +/−:5 charge ratios effect; white columns show +/−:2,5 charge ratios effect; and grey columns show +/−:1 charge ratios effect. A: 10% DSPE-PEG2000, B: 5% DSPE-PEG2000, C: 2% DSPE-PEG2000.

The particle size of lipid-DNA complexes containing PEG-PLs was also stabilized when omitting the final extrusion step (FIG. 6) This stabilizing effect was apparent at different +/− charge ratios and different concentrations of PEG-PLs. In particular, lipid-DNA complexes with high +/− charge ratios were efficiently stabilized, but all of the preparations had mean particle diameters of less than 400 nm and, in most cases, of less than 200 nm as compared with particle sizes of more than 1000 nm in the absence of PEG-PLs (FIGS. 4A–D). The absence of PEG-PL in the complexes resulted in visible flocculation and precipitation after addition of plasmid DNA to the cationic lipids at a final concentration of 200 µg/ml, which prevented meaningful PCS measurements.

Stability studies at 4° C. showed that the extruded complexes remained stable at an average particle diameter of about 170 nm (PCS measurement) for at least 2 months. Furthermore, such complexes allow in vivo transfection via the intratracheal and intravenous route as shown in Example 3. The additives stabilize complexes between cationic lipids and nucleic acids, and allow extrusion of such complexes through membranes of defined pore size without modification of the complexed nucleic acid. Phospholipids derivatized with polyethylene glycol prove to be efficient in preventing aggregation and precipitation of lipid-DNA complexes.

EXAMPLE 2

Transfection of Cells Using Cationic Lipid-Nucleic Acid Complexes

Methods

From an initial 20 ml of cell culture containing $2\times10^6$ cells, $2\times10^4$ cells per well (96 well culture plate) were plated in 200 µl DMEM medium supplemented with glutamine and 10% fetal calf serum on day 1. On day 2, two microtiter plates were prepared: one plate contained different dilutions of plasmid DNA in 70 µl medium without serum per well (starting concentration: 0.16 mg/ml) and one plate contained the lipid suspension in 60 µl per well (starting concentration: 0.187 mg/ml). Both the DNA and the lipids were serial diluted (factor of 2) and the required amount of DNA was transferred into the well containing the required amount of lipids. The medium was removed from the cells by aspiration and the lipid-DNA complexes (100 µl) were transferred onto the cells. After 4 h at 37° C., 5% CO2 and 50 µl of medium containing 30% fetal calf serum were added. On day 3, an additional 100 µl medium containing 10% fetal calf serum were added and on day 4 the cells were inspected microscopically for viability. The transfection was stopped by removing the medium and the cells were washed with 100 µl phosphate-buffered-saline (PBS). After addition of 50 µl lysis buffer (Promega, 5× diluted in water) cells were frozen to −80° C. for at least 15 min. The amount of luciferase produced was determined in 20 µl of the lysis solution for 1 min using the Luciferase Assay System (Promega) in 96 well microtiter plates (Berthold) in the kinetics mode of a Berthold LB 96 P luminometer.

Results

Incorporation of 10 mol % of PEG-PLs completely blocked the in vitro transfection activity of the lipid-DNA complexes in cultured A549 cells (FIGS. 7A and B). This effect may be due to the fact that the PEG-PLs prevent efficient contact between the vector complexes and cells in culture. It was thus even more surprising to find that these vectors allowed transfection in vivo by either the intratracheal (i.t.) or intravenous (i.v.) route of administration (see results below).

EXAMPLE 3

In Vivo Administration of Cationic Lipid-Nucleic Acid Complexes

Methods

Intratracheal injection into mice: 5 to 6 weeks old mice (C57 Black/10 or Balb/c) were anesthetized using Ketamine and 125 μl vector preparations containing 25 μg of pCMV-luc plasmid DNA complexed to cationic lipids at different charge ratios were injected into the trachea. Complexes were not extruded and contained no DSPE-PEG2000. After 48 hours, the mice were sacrificed and the trachea, left and right lungs were removed, frozen in liquid N2 and stored at −70° C.

Intravenous injection into mice: 5 to 6 weeks old mice (C57 Black/10 or Balb/c) were injected with 400 μl vector preparations into the tail vein. Preparations contained 75 μg pCMVluc DNA complexed to cationic lipids at different charge ratios. After seven days, organs (lung, heart, spleen, liver, skeletal muscle) were taken, frozen in liquid N2 and stored at −70° C.

Preparation of Protein Extracts and Determination of Luciferase Activity:

Luciferase extracts were prepared as described (Manthorpe, Human Gene Therapy 4:419–43, 1993) with the following modifications. Frozen tissue was pulverized in pre-cooled mortars on dry ice. The powder was transferred to 1.5 ml Eppendorf tubes and extracted in 500 pi Reporter Lysis Buffer (Promega) using 3 cycles of freeze-thaw in liquid N2 and at 37° C. Lysates were centrifuged at 14,000 rpm for 10 min in an Eppendorf centrifuge at room temperature and supernatants were transferred to new tubes. The pellet was eventually used for DNA extraction. Extracts were frozen in liquid N2 and stored at −70° C. Protein concentrations were determined with the Quantify Protein Assay System (Promega). Luciferase activity was measured in 10 μl aliquots of extracts using the Luciferase Assay System (Promega) in 96 well microliter plates (Berthold) using the kinetics mode of a Berthold LB 96 P luminometer. Luciferase activities were measured on organ samples, i.e., trachea, left and right lung, which were taken from injected mice. After hybridization and lysis in reporter lysis buffer (Promega), 10 or 20 μl aliquots are mixed with 100 μl of substrate (Luciferase Assay System, E1501, Promega). One minute readings were taken on the luminometer according to the manufacturer's protocol. Luciferase activities were calculated either as RLU/mg protein or as fg luciferase/mg protein with the aid of a luciferase standard curve, that was established with purified enzyme (Promega) diluted in a negative tissue extract.

Results

Figure 8:
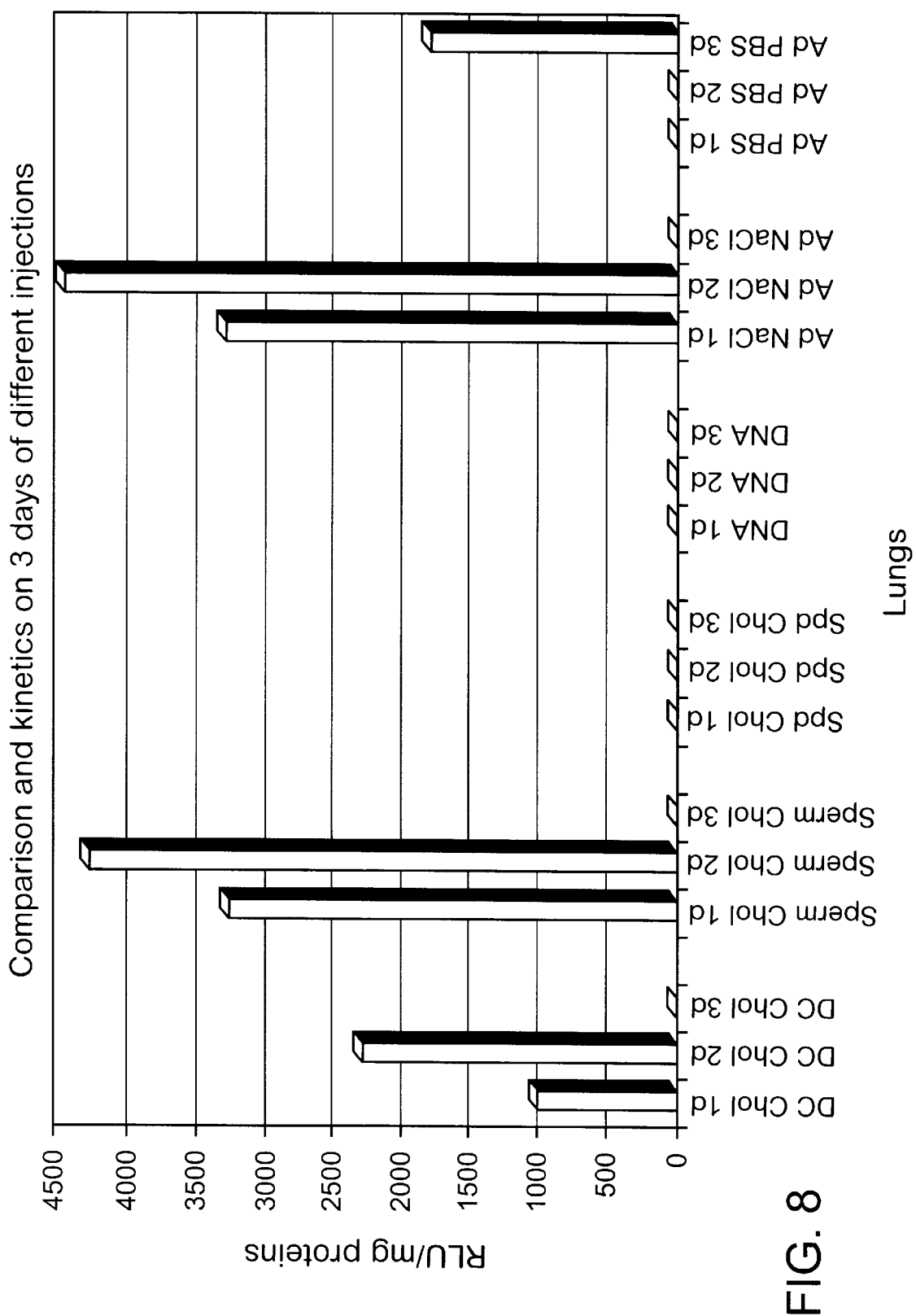
FIG. 8 shows luciferase activity (RLU/mg protein) after intratracheal injection of different cationic lipid-DNA complexes into mice as a function of the day post-injection, compared to the injection of free DNA only or an recombinant adenovirus control.

Intratracheal administration: FIG. 8 summarizes an experiment with different cationic lipids (DC-Chol, spermidinechol, spermine-chol) formulated with the colipid DOPE that were used to complex pCMVluc DNA at a charge ratio of 5:1. The ratio of cationic lipid:DOPE is 1:1 by weight. Lipid-DNA complexes in this experiment were prepared and irrimediately injected i.t. into the test animals to avoid the formation of large aggregates that could reduce the transfection efficiency of the complexes. Luciferase activities were measured as previously described on organ samples, i.e., trachea, right and left lung taken from injected mice 1, 2 and 3 days after i.t. injection, using a recombinant adenovirus containing the luciferase gene as a control.

Luciferase activity could be detected for DC-Chol/DOPE, or spermine-Chol/DOPE complexed DNA at 24 and 48 hrs. The same was true for adenovirus in 0.9% NaCl. No activity was found for free DNA and in this experiment for DNA complexed to spermidine-Chol/DOPE.

Extruded complexes with additives: The next set of experiments tested lipid-DNA formulations having a defined particle size and an increased stability after formulation. For this purpose, complexes were prepared by extrusion which generates particles with an average size of about 200 nm. The addition of DSPE-PEG2000 as a component of lipid-DNA complexes in these formulations was also tested.

Figure 9:
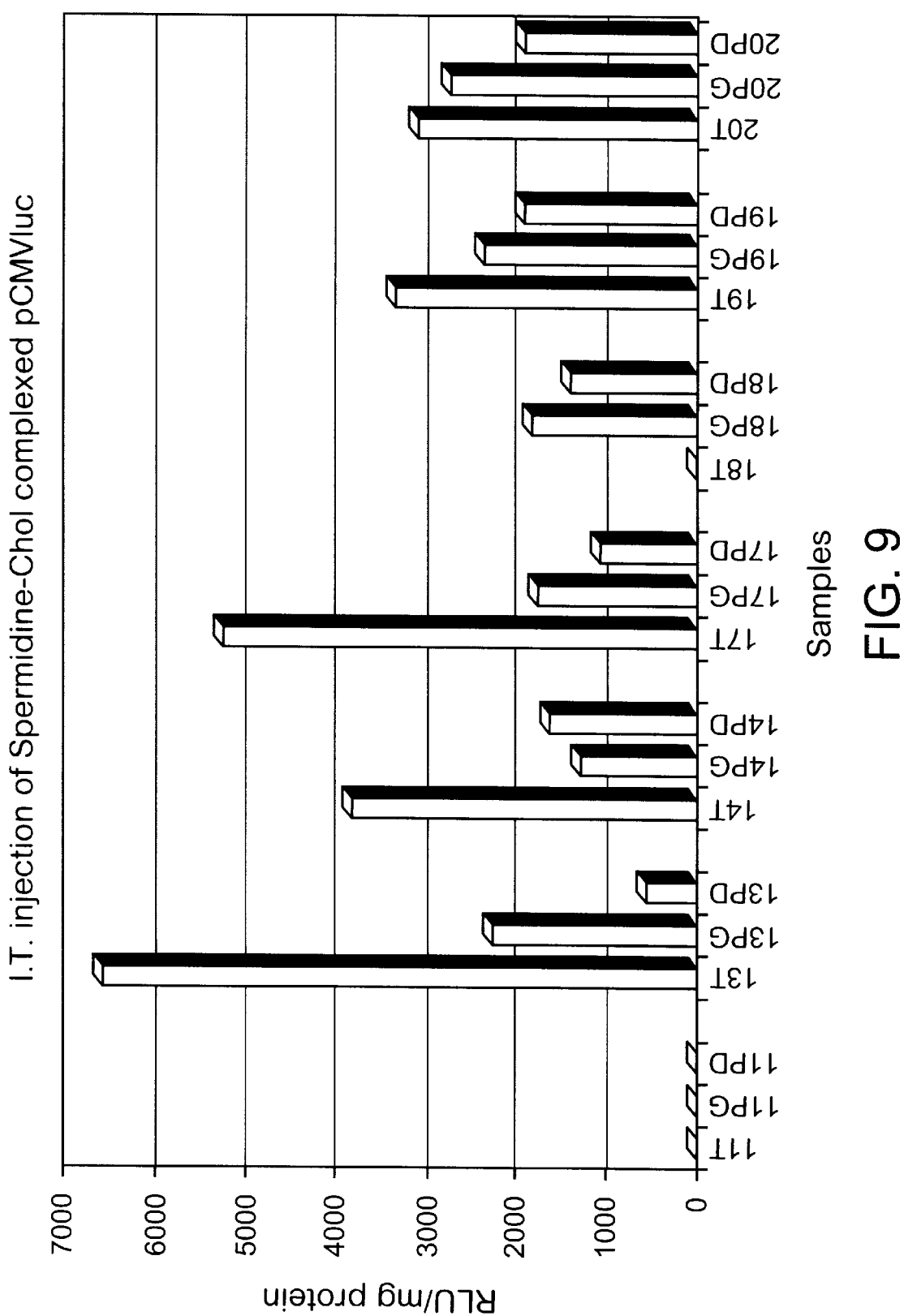
FIG. 9 shows luciferase activity (RLU/mg protein) after intratracheal injection of spermidineChol/DOPE-pCMVluc complexes+10% DSPE-PEG2000 +/− extrusion into mice. Tissue sites of assay for each numbered mouse are as follows: (T:trachea; PG: left lung; PD: right lung).

Spermidine-Chol/DOPE was complexed with 25 pg pCMVluc at a charge ratio of 5:1 in the presence of 10 mol % DSPE-PEG2000. The ratio of cationic lipid:DOPE is 1:1 by weight. Samples were either directly administered by intratracheal injection into 6 weeks old C57 Black/10 mice or size fractionated by extrusion prior to injection. After 48 hours, animals were sacrificed and luciferase activity was determined in trachea (T), left (PG) and right (PD) lungs of each animal. FIG. 9 shows luciferase activities after injection of spermidine-Chol/-DOPE-pCMvluc complexes into mice. Mouse 11 was injected with 25 pg free pCMVluc DNA. No luciferase activity could be detected after 48 h. Mice 13 and 14 received complexes that were not extruded and mice 17, 18, 19 and 20 received complexes after extrusion. Luciferase activities in the range of 1000 to 7000 RLU/mg protein were measured for tracheas and lungs of all mice with the exception of mouse 18 that showed no activity in trachea.

Effect of charge ratio and stabilizing additive: The influence of the charge ratio of spermidine-Chol/DOPE-pCMVluc complexes and the concentration of DSPE-PEG2000 in these complexes was further studied. Spermidine-Chol/DOPE-pCMVluc complexes with charge ratios 5:1, 2.5:1 and 1:1 were prepared. For each charge ratio DSP-PEG2000 was added to 10, 5 or 2 mol %. 48 h after i.t. injection into C57 Black/10 mice, luciferase activities were determined in tracheas and lungs of these animals. Table 1 summarizes the results of this experiment.

TABLE 1

Influence of Charge Ratios and DSPE-PEG2000 Concentration on i.t. activity of Spermidine-Chol/DOPE-pCMVluc complexes

| RATIO | DSPE-PEG2000 mol % | Trachea* RLU/mg protein +/− SD | Lung* RLU/mg protein +/− SD |
|---|---|---|---|
| 5:1 | 10 | 4416 +/− 1472 | 1839 +/− 491 |
|  | 5 | 7200 +/− 1086 | 4173 +/− 34 |
|  | 2 | 0 | 8251 +/− 635 |
| 2.5:1 | 10 | 12007 +/− 473 | 0 |
|  | 5 | 15263 +/− 911 | 0 |
|  | 2 | 7636 +/− 1192 | 0 |
| 1:1 | 10 | 77687 +/− 4956 | 0 |
|  | 5 | 378373 +/− 46162 | 0 |
|  | 2 | 116596 +/− 213 | 0 |

*RLU/mg protein SD of at least three independent measurements of at least two independent mice Luciferase activity in lungs was measurable after injection of complexes with a 5:1 charge ratio. A decrease of DSPE-PEG2000 from 10 to 2 mole resulted in an increase in luciferase activity within this experiment. At lower charge ratios, luciferase activity was no longer detected in the lungs. In tracheas, luciferase activity increased with decreasing charge ratios. The DSPE-PEG2000 concentration is probably also influencing this activity.

One explanation for this is that DSPE-PEG2000 may destabilize the cationic lipid-DNA complexes with respect to how tightly the DNA is bound to and covered by the cationic lipid. This effect would be more important for lower charge ratios. Due to this effect, only complexes with a high charge ratio are stable enough to reach and transfect lung cells. At lower charge ratios, the complexes become unstable and can efficiently transfect cells in the trachea next to the injection site but do not penetrate deep enough into the lung to transfect lung tissues.

Intravenous Administration:

To test the influence of different charge ratios and the presence of DSPE-PEG2000 on formulations for i.v. delivery, 75 μg pCMVluc DNA were complexed at charge ratios 1:2, 1:4 and 1:6 with DC-Chol/DOPE in the presence or absence of 10% DSPE-PEG2000 and i.v. injected in 400 μl volumes. The ratio of cationic lipid:DOPE was 1:1 by weight. The complexes were not extruded.

Figure 10:
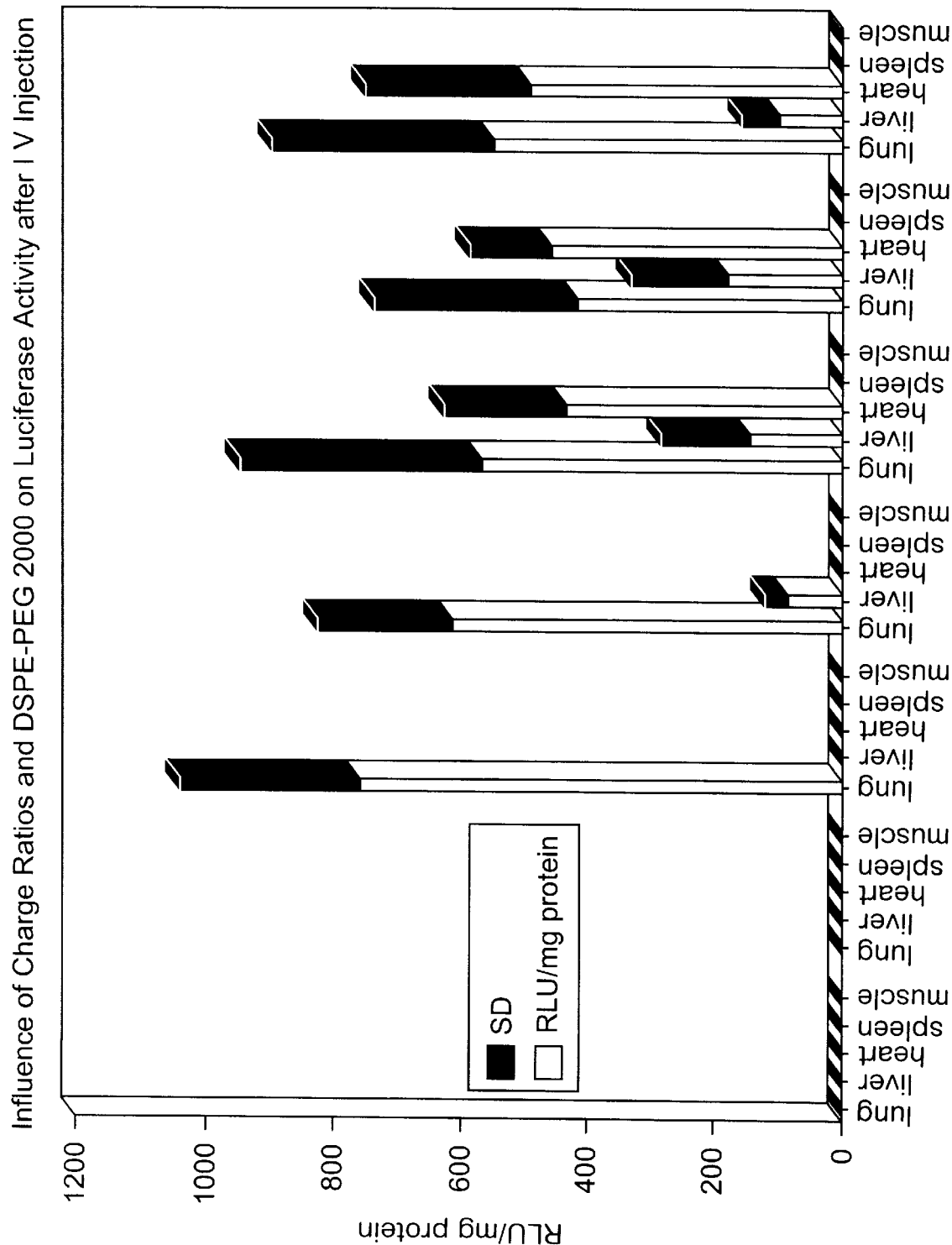
FIG. 10 shows the influence of charge ratios and DSPE-PEG2000 (PEG-PL) on luciferase activity (RLU/mg protein) after intravenous injection of cationic lipid-DNA complexes containing DC-Chol/DOPE into mice, compared to the injection of free DNA. Tissue sites of the assays are shown.
Figure 11:
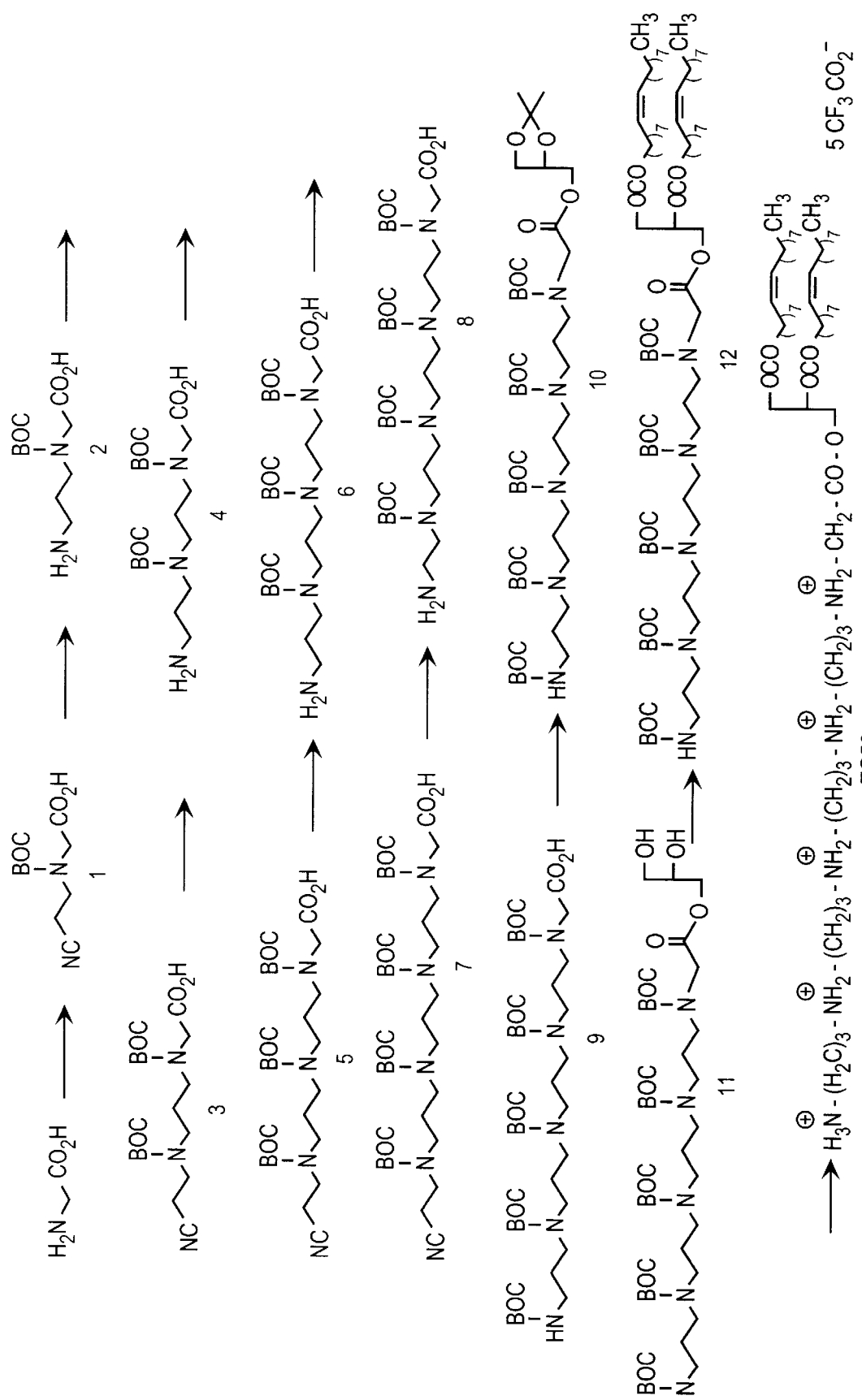
FIG. 11 is a schematic representation of the synthesis of cationic glycerolipid pcTG56.

Luciferase activities were determined seven days later in lung, liver, heart, skeletal muscle and spleen. The results are shown in FIG. 10. Luciferase activity is indicated as RLU/mg protein +/- (standard deviation) for groups of 4 independent mica per formulation. No luciferase activity can be found in muscle and spleen. Low activities are found in heart and liver for charge ratios 1:4 (800 μg total lipid (400 μg DC-Chol):75 μg DNA) and 1:6 (1200:75). In lung relatively high values are detected starting at 1:2 (400:75) charge ratio +10% DSPE-PEG2000.

The ratio of lipids to DNA was changed in these experiments to evaluate the influence of this parameter as well as the presence of DSPE-PEG2000 on in vivo transfection. The rationale behind increasing the amount of lipids was that the DNA might be more stable in vivo and that a more positive charge ratio might lead to a modified tropism of the complexes. It appears from this experiment that higher charge ratios lead to more consistent transfections. It is also noteworthy that the presence of DSPE-PEG2000 prevented visible precipitations which formed in all preparations that did not contain the additive.

EXAMPLE 4

Preparation of Cationic Lipid-Nucleic Acid Complexes Containing Cationic Glycerolipids pcTG56

A. Synthesis of Cationic Glycerolipids pcTG56

PcTG56 has been prepared according to the following protocol (see also FIG. 15)

Cyano Acid 1

A solution of acrylonitrile (9.6 ml, 146 mmoles) in 1,4-dioxane (50 ml) was added dropwise to an ice-cold solution of glycine (10.0 g, 132 mmoles) and of 1N sodium hydroxide (133 ml) in a 1/1 mixture of water and of 1,4-dioxane (200 ml). The reaction was stirred at 0° C. for 1 h and at room temperature for an extra 4 h. A solution of ditertiobutyl dicarbonate (35.0 g, 159 mmoles) in 1,4-dioxare (100 ml) was then added dropwise and the reaction mixture was stirred for 2 h at room temperature. After extraction with ether (2×100 ml), the aqueous phase was acidified (pH 2–3) with 1 N hydrochloric acid and extracted with ethyl acetate (2×100 ml). The combined organic phases were dried with sodium sulfate and concentrated in vacuo. The cyano acid 1 (24.4 g; 81% yield) was obtained as a white solid which was used without further purification. mp=87–89° C.

$^1$H NMR (200 MHz, DO): d 3.88 and 3.87 (2 s, 2H, —$CH_2$—$CO_2H$), 3.48 and 3.45 (2 t, J=6.3 Hz, 2H, —$CH_2$—N(BOC)—), 2.58 and 2.56 (2 t, J=6.3, 6.4Hz, 2H, —$CH_2$—CN), 1.30 and 1.24 (2 s, 9H, t—Bu—).

Amino Acid 2

A solution of cyano acid 1 (11.5 g, 50.4 mmoles) in ethanol (100 ml) containing sodium hydroxide (4.04 g, 100 mmoles) was hydrogenated in the presence of Raney nickel (3.2 g) for 18 h at room temperature. The mixture was carefully filtered on celite and the catalyst washed with methanol (2×30 ml). The filtrate was acidified (Ph 4–5) with 10% aqueous hydrochloric acid and concentrated in vacuo to give a white solid which was dissolved in chloroform (50 ml) to precipitate most of the sodium chloride. After filtration, concentration in vacuo of the filtrate, and recrystallisation in carbon tetrachloride, amino acid 2 (10.4 g; 89%) was obtained. mp=201–202° C.

$^1$H NMR (200 MHz, $D_2O$): d 3.53 (s, 2H, —$CH_2$—$CO_2H$), 3.17 (t, J=6.6 Hz, 2H, —$CH_2$—N(BOC)—), 2.83 (t, J=7.5 Hz, 2H, —$CH_2$—$NH_2$), 1.69 (quint., J=7 Hz, 2H, —$CH_2$—), 1.26 and 1.21 (2 s, 9H, t—Bu—).

Cyano Acid 3

The same procedure as for 1 allowed the obtention of the cyano acid 3 from 2.

$^1$H NMR (200 MHz, $CDCl_3$): d 4.00–3.85 (m, 2H, —$CH_2$—$CO_2H$), 3.55–3.43 (m, 2H, —$CH_2$—$CH_2$—CN), 3.31 (t, J=7.2 Hz, 4H, —$CH_2$—N(BOC)—), 2.61 (m, 2H, —$CH_2$—CN), 1.78 (quint., J=7.2 Hz, 2H, —$CH_2$—), 1.47 and 1.44 (2 s, 18H, t—Bu—).

Amino Acid 4

The amino acid 4 (87% yield; purification by chromatography on a silica gel column, eluent methanol/dichloromethane 3/7, then 6/4) was obtained from 3 by the same procedure as the amino acid 2. mp=189–190° C.

$^1$H NMR (200 MHz, $D_2O$): d 3.57 and 3.54 (2 s, 2H, —$CH_2$—$CO_2H$), 3.2–3.0 (m, 6H, —$CH_2$—N(BOC)—), 2.80 (t, J=7.7 Hz, 2H, —$CH_2$—$NH_2$), 1.80–1.50 (m, 4H, —$CH_2$—), 1.27 and 1.22 (2 s, 18H, t—Bu—).

Cyano Acid 5

The same procedure as for 1 allowed the obtention of the cyano acid 5 from 4.

$^1$H NMR (200 MHz, $CDCl_3$): d 3.85 (br s, 2H, —$CH_2$—$CO_2H$), 3.47 (t, J=6.6 Hz, 2H, —$CH_2$—$CH_2$—CN), 3.35–3.05 (m, 8H, —$CH_2$—N(BOC)—), 2.60 (m, 2H, —$CH_2$—CN), 1.85–1.60 (m, 4H, —$CH_2$—), 1.46 and 1.44 (2 s, 27H, t—Bu—).

Amino Acid 6

The amino acid 6 (83% yield; purification by chromatography on a silica gel column, eluent methanol/dichloromethane 3/7 then 6/4) was obtained from 5 by the same procedure as compound 2.

$^1$H NMR (200 MHz, $D_2O$): d 3.76 and 3.73 (2 s, 2H, —$CH_2$—$CO_2H$), 3.25–2.75 (m, 12H, —$CH_2$—N(BOC)— and —$CH_2$—$NH_2$), 1.85–1.50 (m, 6H, —$CH_2$—), 1.28 and 1.23 (2 s, 27H, t—Bu—).

Cyano Acid 7

The same procedure as for 1 allowed the obtention of the cyano acid 7 from 6.

$^1$H NMR (200 MHz, $CDCl_3$): d 3.95 and 3.87 (2 br s, 2H, —$CH_2$—$CO_2H$), 3.47 (t J=6.5 Hz, 2H, —$CH_2$—$CH_2$—CN), 3.40–3.05 (m, 12H, —$CH_2$—N(BOC)—), 2.61 (m, 2H, —$CH_2$—CN), 1.90–1.60 (m, 6H, —$CH_2$—), 1.47, 1.45 and 1.44 (3 s, 36H, t—Bu—).

Amino Acid 8

The amino acid 8 (71% yield; purification by chromatography on a silica gel column, eluent methanol/dichloromethane 1/9 then 3/7) was botained from 7 by the same procedure as compound 2.

$^1$H NMR (200 MHz, D$_2$O): d 3.76 and 3.73 (2 s, 2H, —CH$_2$—CO$_2$H), 3.25–2.75 (m, 12H, —CH$_2$—N(BOC)— and —CH$_2$—NH$_2$), 1.85–1.50 (m, 6H, —CH$_2$—), 1.28 and 1.23 (2 s, 27H, t—Bu—).

Acid 9

Ditertiobutyldicarbonate (1.19 g, 5.45 mmoles) dissolved in CH$_2$Cl$_2$ (5 ml) was added to a solution of compound 8 (3.20 g, 4.55 mmoles) and triethylamine (0.95 ml, 6.83 mmoles) in CH$_2$Cl$_2$ (45 ml). The mixture was stirred for 16 h at room temperature, then acidified to pH 3 with HCl 5% and extracted twice with CH$_2$Cl$_2$ (30 ml). The organic phase was washed with watter (20 ml), dried over sodium sulfate, and concentrated to give a colourless oil which was purified by silica gel column chromatography (methanol/dichloromethane 5/95 then 10/90) to give compound 9 (3.37 g, 92%).

$^1$H NMR (200 MHz, CDCl$_3$): d 3.85 (m, 2H, —CH$_2$—CO$_2$H), 3.45–3.05 (m, 16H, —CH$_2$—N(BOC)—), 1.85–1.60 (m, 8H, —CH$_2$—), 1.45, 1.44 and 1.43 (3 s, 36H, t—Bu).

Ester 10

Dicyclohexylcarbodiimide (0.53 g, 2.59 mmoles) in dry dichloromethane (1 ml) was added to a solution of the acid 9 (1.60 g, 1.99 mmoles), of (S)-(+)-2,2-dimethyl-1,3-dioxolane-4-methanol (0.34 g, 2.59 mmoles) and of 4-(dimethylamino)pyridine (24 mg, 0.2 mmole) in dry dichloromethane (4 ml). The reaction mixture was stirred for 16 h at room temperature. Then the precipitate of dicyclohexylurea was removed by filtration and the filtrate was concentrated in vacuo and chromatographed on a silica gel column (eluent ether/hexane 5/5 then 6/4) to give the ester 10 (1.73 g; 95%)

$^1$H NMR (200 MHz, CDCl$_3$): d 4.35–4.04 (m, 4 H), 3.99–3.92 (2 S, 2H, —CH$_2$—CO), 3.74 (m, 1H), 3.30–3.00 (m, 16H, —CH$_2$—N(BOC)—), 1.85–1.55 (m, 8H, —CH$_2$—), 1.46, 1.45, 1.44 and 1.42 (4 s, 48H, t—Bu— and Me—), 1.36 (s, 3H, Me—).

Dihydroxyester 11

A solution of ester 10 (1.55 g, 1.69 mmoles) and of 1H hydrochloric acid (0.68 ml) in methanol (29 ml) was stirred for 16 h at room temperature. Triethylamine (1 ml) was then added to the solution until neutral. Evaporation in vacuo and silica gel column chromatography (eluent: methanol/dichloromethane 5/95) gave the dihydroxyester 11 (1.23 g; 83%) as a colourless oil.

$^1$H NMR (200 MHz, CDCl$_3$): d 4.25 (m, 2H, —CH$_2$—OCO—), 4.00–3.40 (m, 5H, CH—OH, —CH$_2$OH, and —CH$_2$—CO$_2$—), 3.40–3.00 (m, 116H, CH$_2$—N(BOC)—), 1.90–1.6 (m, 8H, —CH$_2$—), 1.46, 1.45, 1.44 and 1.42 (4 s, 45H, t—Bu—).

Triester 12

Dicyclohexylcarbodiimide (0.71 g, 3.42 mmoles) in dry dichloromethane (1 ml) was added to a solution of dihydroxyester 11 (1.00 g, 1.14 mmoles), oleic acid (0.97 g, 3.42 mmoles) and 4-(dimethylamino)pyridine (14 mg, 0.11 mmole) in dry dichloromethane (3 ml). The reaction mixture was stirred for 16 h at room temperature. Then the precipitate of dicyclohexylurea was removed by filtration and the filtrate was concentrated in vacuo and chromatographed on a silica gel column (eluent: ether/hexane 4/6) to give the triester 12 (754 mg; 47%) as colourless oil.

$^1$H NRM (200 MHz, CDCl$_3$): d 5.34 (m, 4H, —CH=), 5.26 (m, 1H, CH—OCO—), 4.40–4.05 (m, 4H, —CH$_2$—OCO—), 3.95 and 3.89 (2 m, 2H, —N(BOC)—CH$_2$—CO$_2$—), 3.35–3.00 (m, 16H, —CH$_2$—N(BOC)—), 2.31 (t, J 7.5 Hz, 4H, —CH$_2$—CO$_2$—), 2.01 (m, 8H, allylic H), 1.85–1.50 (m, 12H, —CH$_2$—), 1.46, 1.44, 1.43 and 1.41 (4 s, 45H, t—Bu—), 1.30 and 1.27 (2 br s, 44H, —CHI-), 0.88 (t, J=6.4 Hz, 6H, Me—).

Cationic Glycerolipids pcTG56

The triester 12 (0.52 g, 0.37 mmole) in dry dichloromethane (1 ml) was treated for 3 h with a 1/1 mixture of trifluoroacetic acid and dry dichloromethane (74 ml) at 0° C. Hexane (100 ml) was then added and the mixture was evaporated in vacuo to leave a thin film which was suspended (vortex) in distilled ether. Filtration gave a white powder which was washed with ether and dried in vacuo to give the lipid 13 (510 mg; 93 z).

$^1$H NMR (200 MHz, CDCl$_3$—CF$_3$CO$_2$D): d 5.36 (m, 5H, —CH= and CH—OCO—), 4.60–4.15 (m, 4H, —CH$_2$—OCO—), 4.00 (s, 2H, —NH$_2^+$—CH$_2$—CO$_2$—), 3.45–3.10 (m, 16H, —CH$_2$—NH$_2^+$—), 2.41 (t, J=7.5 Hz, 4 H, —CH$_2$—CO$_2$—), 2.28 (m, 8H, —CH$_2$—CH$_2$—NH$_2^+$—), 2.01 (m, 8H, allylic H), 1.61 (m, 4H, —CH$_2$—CH$_2$—CO$_2$—), 1.30 and 1.27 (2 4, 44 H, —CH$_2$—), 0.87 (t, J=6.4 Hz, 6H, Me—).

B. Formulation of DNA-Lipid Complexes Containing pcTG56

DNA-lipid complexes were prepared with a final concentration of 0.5 or 1 mg/ml DNA at charge ratio 5 (ratio between positive charges carried by the cationic lipid and negative charges carried by the DNA) with an equimolar amount of dioleyl-phosphatidylethanolamine (DOPE). The amount of cationic lipid to be added was determined based on its molecular weight, the number of positive charges per molecule and the desired charge ratio. As an example, to obtain a complex of pcTG56/DOPE at a charge ratio 5 and a final DNA concentration of 0.5 mg/ml, the following calculation applies 0.5 mg/ml DNA correspond to a concentration of 0.5/330 mmoles/ml=1.5 mmoles/ml negative charges (330Da is taken as the average molecular weight of a nucleotide). To obtain a complex at charge ratio 5, the concentration of positive charges must be 7.5 mmol/ml (molecular weight of pcTG56 in the form of its trifluoroacetate salt: 1476 g/mol; 5 positive charges per molecule) or 1.5 mmol/ml pcTG56 (2.2 mg/ml). To reach an equimolar concentration, 1.5 mmol of DOPE were added (molecular weight 744 g/mol; final concentration of 1.1 mg/ml). Distearoyl-phosphatidylethanolamine (DSPE) coupled to polyethyleneglycol of an average molecular weight of 5000 Da (PEG5000) (Avanti Polar Lipids, Alabaster, Ala., U.S.A.; Ref. 880220) (average molecular weight taken to be 5750 g/mol) was added to reach the required final concentrations of 2, 5 or 10 mol % with respect to the total amount of lipid.

Lipids were mixed from their respective solutions in chloroform/methanol (1/1). The lipid solution was dried (200 mbar, 45° C., 45 min) with vortexing (40 revolutions per minute) (Labconco, Rapidvap, Uniequip, Martinsried, Germany) and the lipid film was taken up in dimethylsulfoxide (DMSO)/ethanol (1/1). As an example, 2.2 mg pcTG56 and 1.1 mg DOPE were taken up in 45 ml dimethylsulfoxide/ethanol. 175 ml 20 mM (N-[2-hydroxyethyl]piperazine-N'-[2-ethanesulfonic acid]) (HEPES), pH 7.5 were added to reach a final concentration of 10 mg/ml in cationic lipid. 500 ml plasmid DNA (pTG11033; 1 mg/ml in 10 mM (tris)[hydroxymethyl] aminomethane) (Tris), 1 mm ethylenediaminetetraacetic acid (EDTA), pH 7.5) were diluted with 280 ml 20 mM HEPES, ph 7.5 220 ml of the above lipid suspension were added to this solution by rapid aspiration-pipetting (10-times) to obtain 1 ml of the final complex at a DNA concentration of 0.5 mg/ml and a charge ratio of 5. Preparations at 1 mg/ml DNA with and without DSPE-PEG5000 were reconstituted using the same method by adjusting the amounts of DNA, lipids and stabilizer accordingly. The obtained lipid-DNA complexes were stored at 4° C.

Results

Particle size of the cationic lipid-nucleic acid complexes was measured by photon-correlation spectroscopy and is given as the mean value weight normalized (see Example 1). Table 2 summarizes the results of this experiment.

TABLE 2

Influence of the DNA concentration and of the % of DSPE-PEG5000 on particles size stability

| Preparation Day after preparation (storage 4° C.) | Charge Ratio +/− | Mean Particle Size (nm) | | |
|---|---|---|---|---|
| | | Day 1 | Day 7 | Day 10 |
| 1 mg/ml DNA; 2 mol % DSPE-PEG5000 | 5 | 234 | — | — |
| 1 mg/ml DNA; 2 mol % DSPE-PEG5000 20% DMSO | 5 | 96 | — | — |
| 0.5 mg/ml DNA; 2 mol % DSPE-PEG5000 | 5 | 150 | 141 | 131 |
| 0.5 mg/ml DNA; 5 mol % DSPE-PEG5000 | 5 | 66 | 60 | 105 |
| 0.5 mg/ml DNA; 10 mol % DSPE-PEG5000 | 5 | 68 | 69 | 75 |

The results shown above extend our previous findings in that:

a) lipid-DNA complexes can be formed with higher (1 mg/ml) DNA concentration (previously 0.2 mg/ml);

b) that DSPE-PEG is compatible with lipids of other structural classes such as cationic glycerolipids (pcTG56), and c) that DSPE-PEG5000 can replace DSPE-PEG2000.

In addition, they show that our methodology is compatible with other additives such as DMSO, which may enhance in vivo gene transfer.

What is claimed is:

1. A method for preparing an homogenous suspension of stable lipid-nucleic acid complexes or particles, comprising:
   a) combining one or more cationic lipids, one or more colipids, and one or more stabilizing additives to form a lipid suspension,
   b) combining the lipid suspension with a nucleic acid to form a complex or a particle, and optionally
   c) subjecting the complex or particle to a sizing procedure.

2. The method of claim 1, further comprising the step of subjecting the lipid suspension to a sizing procedure to form a lipid suspension of particles of homogenous size.

3. The method of claim 1, wherein the sizing procedure comprises extruding the lipid-nucleic acid complexes or particles through a membrane of defined pore diameter.

4. The method of claim 3, wherein the lipid-nucleic acid complexes or particles are extruded through membranes having pore sizes in the range of 50 to 500 nm.

5. The method of claim 1, wherein the lipid-nucleic acid complexes or particles in the homogenous suspension have a particle size of 500 nm or less.

6. The method of claim 1, wherein the lipid-nucleic acid complexes or particles in the homogeneous suspension have a particle size of 200 nm or less.

7. The method of claim 1, wherein the cationic lipid or lipids are selected from the group consisting of spermidine-cholesterol, spermine-cholesterol, 3β[N-(N',N'-dimethylaminoethane)-carbamoyl] cholesterol, dioctadecylamidoglycylspermine, and mixtures thereof.

8. The method of claim 1, wherein the colipid is dioleoylphosphatidylethanolamine.

9. The method of claim 1, wherein the stabilizing additive is polyethylene glycol coupled to a colipid.

10. The method of claim 1, wherein the stabilizing additive is selected from the group consisting of perfluorinated or partially fluorinated alkyl chains coupled to colipid.

11. The method claim 1, wherein the stabilizing additive is polyglucuronic acid coupled to a colipid.

12. The method of claim 1, wherein the stabilizing additive is distearoylphosphatidylethanolamine-polyethylene glycol.

13. The method of claim 9, wherein the moiety is a phospholipid.

14. The method of claim 13, wherein the moiety is a zwitterionnic phospholipid.

15. The method of claim 1, wherein the nucleic acid is selected from the group consisting of genomic DNA, cDNA, synthetic DNA, RNA, mRNA, ribozymes, antisense RNA and oligonucleotides.

16. The method of claim 15, wherein the nucleic acid comprises a plasmid.

17. An homogenous suspension of stable lipid-nucleic acid complexes or particles, produced by:
   a) combining one or more cationic lipids, one or more colipids, and one or more stabilizing additives to form a lipid suspension,
   b) combining the lipid suspension with a nucleic acid to form a complex or a particle, and optionally
   c) subjecting the complex or particle to a sizing procedure.

18. The suspension of claim 17, wherein the lipid suspension of step a) is subjected to a sizing procedure to form a lip suspension of particles of homogenous size.

19. The suspension of claim 17, wherein the sizing procedure comprises extruding the lipid-nucleic acid complexes or particles through a membrane of defined pore diameter.

20. The suspension of claim 17, wherein the cationic lipids include mixtures of cationic lipids.

21. The suspension of claim 17, wherein the complexes or particles in the homnogeneous suspension have a particle size of 500 nm or less.

22. The suspension of claim 17, wherein the complexes or particles in the homogeneous suspension have a particle size of 200 nm or less.

23. A lipid-nucleic acid complex comprising one or more cationic lipids, one or more colipids, one or more stabilizing additives, and a nucleic acid component.

24. The complex of claim 23, wherein the complex has a particle size of 500 nm or less.

25. The complex of claim 23, wherein the complex has a particle size of 200 nm or less.

26. A pharmaceutical composition comprising the suspension of claim 17 and a pharmaceutically acceptable carrier.

27. A pharmaceutical composition comprising the complex of claim 23 and a pharmaceutically acceptable carrier.

28. A method for the delivery of a nucleic acid to the cells of an individual in need of such nucleic acid, comprising administering the composition of claim 26 to the cells of such an individual.

29. The method of claim 28, wherein the nucleic acid is selected from the group consisting of genomic DNA, cDNA, synthetic DNA, RNA, mRNA, ribozymes, antisense RNA and oligonucleotides.

30. The method of claim 29, wherein the nucleic acid comprises a plasmid.

31. The method of claim 2, wherein the sizing procedure comprises extruding the lipid suspension through a membrane of defined pore diameter.

32. The method of claim 31, wherein the lipid suspension is extruded through membranes having pore sizes in the range of 50 to 500 nm.

33. The suspension of claim 18, wherein the sizing procedure comprises extruding the lipid suspension through a membrane of defined pore diameter.

34. The suspension of claim 19, wherein the lipid-nucleic acids complexes or particles are extruded through membranes having pore sizes in the range of 50 to 500 nm.

35. The suspension of claim 33, wherein the lipid suspension is extruded through membranes having pore sizes in the range of 50 to 500 nm.

* * * * *